United States Patent
Zhu et al.

(10) Patent No.: US 11,085,942 B2
(45) Date of Patent: Aug. 10, 2021

(54) CHEMILUMINESCENCE DETECTOR, CONSUMABLE BOX AUTOMATIC TRANSMISSION DEVICE AND TRANSMISSION METHOD THEREOF

(71) Applicant: Shenzhen New Industries Biomedical Engineering Co., Ltd., Guangdong (CN)

(72) Inventors: Liang Zhu, Guangdong (CN); Li Yin, Guangdong (CN); Shiming Feng, Guangdong (CN); Guoyao He, Guangdong (CN); Yi Hu, Guangdong (CN); Dingping Ban, Guangdong (CN); Lina Lin, Guangdong (CN)

(73) Assignee: Shenzhen New Industries Biomedical Engineering Co., Ltd., Shenzhen (CN)

( * ) Notice: Subject to any disclaimer, the term of this patent is extended or adjusted under 35 U.S.C. 154(b) by 357 days.

(21) Appl. No.: 16/178,623

(22) Filed: Nov. 2, 2018

(65) Prior Publication Data
US 2019/0137531 A1  May 9, 2019

(30) Foreign Application Priority Data

Nov. 9, 2017  (CN) .......................... 201711098344.0

(51) Int. Cl.
*G01N 35/04* (2006.01)
*B01L 9/06* (2006.01)
(Continued)

(52) U.S. Cl.
CPC ................ *G01N 35/04* (2013.01); *B01L 9/06* (2013.01); *G01N 21/76* (2013.01); *B01L 9/52* (2013.01);
(Continued)

(58) Field of Classification Search
CPC ........ G01N 35/04; G01N 21/76; G01N 33/53; G01N 2035/0494; G01N 2035/0425;
(Continued)

(56) References Cited

U.S. PATENT DOCUMENTS 7,360,984 B1 * 4/2008 Sugiyama ............... B01L 9/543
                                                         414/798.1
8,118,153 B2 * 2/2012 Yamasaki ............ G01N 35/028
                                                         198/468.6

(Continued)

*Primary Examiner* — Samuel P Siefke
*Assistant Examiner* — Henry H Nguyen
(74) *Attorney, Agent, or Firm* — Yu Gang

(57) ABSTRACT

The present disclosure provides a consumable box automatic transmission device. The consumable box automatic transmission device includes a consumable box storage mechanism, configured to load and store consumable boxes, and a consumable box lifting mechanism, located above the consumable box storage mechanism; the consumable box lifting mechanism is able to lift the consumable boxes; the consumable box storage mechanism and the consumable box lifting mechanism is able to respectively store and transmit the consumable boxes; the consumable box storage mechanism is able to transmit the consumable boxes to the bottom of the consumable box lifting mechanism; and the consumable box lifting mechanism receives the consumable boxes at a bottom and lifts the consumable boxes to a top layer of the consumable box lifting mechanism. In this way, parallel consumable box transmission can be achieved, and continuous consumable box conveyance is achieved, thereby reducing manual care or frequent manual operation.

15 Claims, 10 Drawing Sheets

(51) Int. Cl.

| | | |
|---|---|---|
| *B01L 9/00* | (2006.01) | |
| *B65G 1/02* | (2006.01) | |
| *B65G 1/04* | (2006.01) | |
| *B65G 1/12* | (2006.01) | |
| *G01N 21/76* | (2006.01) | |
| *G01N 33/53* | (2006.01) | |

(52) U.S. Cl.
CPC ... *B01L 2200/087* (2013.01); *B01L 2200/143* (2013.01); *B01L 2200/18* (2013.01); *B65G 1/02* (2013.01); *B65G 1/04* (2013.01); *B65G 1/12* (2013.01); *G01N 33/53* (2013.01); *G01N 2035/0422* (2013.01); *G01N 2035/0425* (2013.01); *G01N 2035/0475* (2013.01); *G01N 2035/0482* (2013.01); *G01N 2035/0494* (2013.01)

(58) Field of Classification Search
CPC ... G01N 2035/0482; G01N 2035/0475; G01N 2035/0422; B01L 9/06; B01L 2200/18; B01L 2200/143; B01L 2200/087; B01L 9/52; B65G 1/02; B65G 1/04; B65G 1/12
See application file for complete search history.

(56) References Cited

U.S. PATENT DOCUMENTS

2008/0028835 A1* 2/2008 Higuchi ............... G01N 35/028
                                                                  73/53.01
2017/0254826 A1* 9/2017 Eberle .............. G01N 35/00871

* cited by examiner

CHEMILUMINESCENCE DETECTOR, CONSUMABLE BOX AUTOMATIC TRANSMISSION DEVICE AND TRANSMISSION METHOD THEREOF

TECHNICAL FIELD

The present disclosure relates to the technical field of medical detection devices, and more particularly, to a chemiluminescence detector, a consumable box automatic transmission device and a transmission method thereof.

BACKGROUND

Chemiluminescence immunoassay is an in-vitro detection analysis technology in combination of antigen-antibody immunoreaction and luminous reaction. With an immunology theory as a basis and a luminous marker as a tracing signal, and through collecting an optical signal to detect multiple markers, it has the advantages of high sensitivity, low nonspecific adsorption and high accuracy. With the high-speed development of biomedical equipment, certain conditions for implementing complete automation of a chemiluminescence detector have been achieved.

Currently, a chemiluminescence detector mainly includes a consumable box feeding system, a sample adding system, a luminous detection system, a control system and a software system. The consumable box feeding system is an indispensible part of the instrument and mainly includes a loading transmission system and a storage device. In large hospitals, as there is a wide variety of immunoassay items and a large number of to-be-tested samples, consumable boxes need to be frequently added into the storage device. Thus, excessive manual operation and manual care is demanded and safety is lowered. Besides, the storage device is large in plane layout and small in storage capacity, thereby lowering the automation degree of the whole analyzer and affecting the detection efficiency of the instrument.

SUMMARY

In view of this, for the problems that the safety is low and the detection efficiency is affected due to the fact that consumable boxes need to be frequently added at present, it is necessary to provide a consumable box automatic transmission device capable of implementing continuous consumable box loading, preventing frequent consumable box adding and guaranteeing the transmission safety and the detection efficiency, a transmission method using the consumable box automatic transmission device, and a chemiluminescence detector including the consumable box automatic transmission device.

The above objective is implemented by the following technical solutions.

A consumable box automatic transmission device includes:

a consumable box storage mechanism, configured to load and store consumable boxes; and a consumable box lifting mechanism, located above the consumable box storage mechanism; the consumable box lifting mechanism is able to lift the consumable boxes;

the consumable box storage mechanism and the consumable box lifting mechanism is able to respectively store and transmit the consumable boxes; the consumable box storage mechanism is able to transmit the consumable boxes to the bottom of the consumable box lifting mechanism, and the consumable box lifting mechanism receives the consumable boxes at a bottom and lifts the consumable boxes to a top layer of the consumable box lifting mechanism.

In an embodiment, the consumable box lifting mechanism includes a lifting transmission structure; the lifting transmission structure can support multiple consumable boxes therein in a layered manner and is able to drive multiple consumable boxes to move synchronously; the consumable box storage mechanism includes a storage transmission structure; and the storage transmission structure are able to store multiple consumable boxes placed in a laminated manner, and drive multiple consumable boxes to move synchronously, and are able to transmit the consumable boxes to the lifting transmission structure one by one.

In an embodiment, the consumable box storage mechanism includes a storage frame structure and a storage drive structure; the storage drive structure is provided on the storage frame structure; the storage transmission structure is provided in the storage frame structure in a rise-fall manner; the storage drive structure is in transmission connection with the storage transmission structure; and the storage drive structure drives the storage transmission structure, thereby driving multiple consumable boxes to rise or fall in the storage frame structure.

In an embodiment, the consumable box lifting mechanism includes a lifting frame structure and a lifting drive structure; the lifting drive structure is provided on the lifting frame structure; the lifting drive structure is in transmission connection with the lifting transmission structure; the lifting transmission structure is provided in the lifting frame structure in a rise-fall manner;

the lifting drive structure drives the lifting transmission structure, thereby driving multiple consumable boxes to rise or fall in the lifting frame structure; and the storage transmission structure drives multiple consumable boxes to rise, and conveys the consumable boxes to the lifting transmission structure.

In an embodiment, the storage transmission structure includes a storage rise-fall component and a storage support portion provided on the storage rise-fall component; the storage rise-fall component is movably provided on the storage frame structure;

Multiple consumable boxes are able to be provided on the storage support portion in a laminated manner; and the storage drive structure drives the storage rise-fall component, thereby driving the storage support portion to rise or fall.

In an embodiment, the consumable box storage mechanism further includes a storage detection structure; the storage detection structure is provided in the storage frame structure;

the storage detection structure includes a first storage detection unit; a detection area of the first storage detection unit is located at a top layer of the storage frame structure; and the first storage detection unit is able to detect whether there are one or more consumable boxes in the detection area.

In an embodiment, the lifting frame structure includes a lifting border component and multiple lifting surrounding plates; the lifting drive structure is mounted on the lifting border component; the lifting transmission structure is mounted in the lifting border component; and the multiple lifting surrounding plates are arranged oppositely on two sides of the lifting border component.

In an embodiment, the lifting frame structure further includes multiple lifting side plates; and the multiple lifting side plates are arranged oppositely on the other two sides of the lifting border component.

In an embodiment, the storage detection structure further includes a second storage detection unit; the second storage detection unit is provided on the storage frame structure; and a detection area of the second storage detection unit is located under the detection area of the first storage detection unit.

In an embodiment, a movement distance that the storage transmission structure moves from the detection area of the second storage detection unit to the detection area of the first storage detection unit is a height of one consumable box along a rise-fall direction.

In an embodiment, the lifting transmission structure includes two rotating components and multiple rotating support portions; the two rotating components are symmetrically arranged in the lifting frame structure; multiple rotating support portions are respectively provided on the two rotating components, and multiple rotating support portions on each rotating components are arranged intervals along a rise-fall direction;

the lifting drive structure drives the rotating components, thereby driving multiple rotating support portions to move synchronously; and the rotating support portions respectively drive the consumable boxes supported by the rotating support portions to rise or fall.

In an embodiment, the two rotating components are respectively provided on two opposite sides of the lifting frame structure; and the two opposite rotating support portions on the two rotating components can support two ends of each of the consumable boxes.

In an embodiment, each of the rotating components includes a rotating belt and two rotating shafts, the two rotating shafts are rotatably provided on the lifting frame structure, and one end of one rotating shaft stretches out of the lifting frame structure and is in transmission connection with the lifting drive structure; and the lifting drive structure drives the rotating shafts, thereby driving the rotating belts to rotate.

In an embodiment, multiple rotating support portions are uniformly arranged along the periphery of the two rotating belts; and the rotating support portions at corresponding positions on the two rotating belts are arranged in a coplanar manner.

In an embodiment, the consumable box lifting mechanism further includes a lifting detection structure; the lifting detection structure is provided on the lifting frame structure;

the lifting detection structure includes a lifting locating unit; the lifting locating unit is provided on the lifting frame structure; and the lifting locating unit is matched with the rotating support portions, and carries out initial location to the rotating support portions.

In an embodiment, the lifting detection structure further includes a first lifting detection unit; a detection area of the first lifting detection unit is located at a top layer of the lifting frame structure; the rotating components drive the rotating support portions to move to the detection area of the first lifting detection unit, and the first lifting detection unit is able to detect whether there are one or more consumable boxes on the rotating support portions in the detection area.

In an embodiment, the lifting detection structure further includes a second lifting detection unit; a detection area of the second lifting detection unit is located at a bottom layer of the lifting frame structure; the rotating components drive the rotating support portions to move to the detection area of the second lifting detection unit; and the second lifting detection unit is able to detect whether there are one or more consumable boxes on the rotating support portions in the detection area.

In an embodiment, the consumable box automatic transmission device further includes a drawer mechanism; the consumable box storage mechanism is provided in the drawer mechanism; and the drawer mechanism is able to drive the consumable box storage mechanism to move, so that the consumable box storage mechanism is abutted with or separated from the consumable box lifting mechanism.

In an embodiment, the consumable box storage mechanism further includes a master control button, a rise control button and a fall control button; the rise control button, the fall control button and the master control button all are provided on the storage frame structure, and are electrically connected with the storage transmission structure; the rise control button and the fall control button can control the storage transmission structure to switch between a manual mode and an automatic mode; when the storage transmission structure is in the manual mode, the rise control button controls the storage transmission structure to rise, and the fall control button controls the storage transmission structure to fall; when the storage transmission structure is in the automatic mode, the storage transmission structure automatically rises and falls; and he master control button is configured for on-off control.

In an embodiment, the consumable box automatic transmission device further includes a push mechanism; the push mechanism is provided on the consumable box lifting mechanism; and the push mechanism is able to push each of the consumable boxes at the top layer of the consumable box lifting mechanism to a preset position.

In an embodiment, the consumable box automatic transmission device further includes a consumable box recycling mechanism; the consumable box recycling mechanism is located under the preset position; and the consumable box recycling mechanism is able to recycle each of the consumable boxes at the preset position.

A consumable box automatic transmission method is applied to a consumable box automatic transmission device; the consumable box automatic transmission device includes a consumable box storage mechanism and a consumable box lifting mechanism; the consumable box storage mechanism is capable of conveying consumable boxes to the consumable box lifting mechanism; and the consumable box automatic transmission method includes the following steps:

the consumable box storage mechanism drives each of the consumable boxes to rise and move to the bottom of the consumable box lifting mechanism;

the consumable box lifting mechanism receives the consumable boxes at a bottom; and the consumable box lifting mechanism transmits the consumable boxes to a lesser top layer of the consumable box lifting mechanism.

In an embodiment, the consumable box storage mechanism includes a storage detection structure and a storage transmission structure configured to transmit the consumable boxes; the storage detection structure includes a first storage detection unit; the first storage detection unit is located at a top layer of the consumable box storage mechanism; and the consumable box automatic transmission method further includes a step that the consumable boxes are loaded into the consumable box storage mechanism and includes the following steps:

the storage transmission structure is controlled to rise or fall along the height direction of the consumable box storage mechanism according to a detection signal sent by the first storage detection unit;

the storage transmission structure is controlled to move upward for one layer along the height direction of the consumable box storage mechanism whenever the first storage detection unit does not detect any consumable box;

if the first storage detection unit does not detect any consumable box all the time and the storage transmission structure moves to the top layer of the consumable box storage mechanism, the storage transmission structure stops moving, and the consumable boxes are loaded onto the storage transmission structure; and whenever the first storage detection unit detects one or more consumable boxes, the storage transmission structure is controlled to move downward for one layer along the height direction of the consumable box storage mechanism, and the consumable boxes are loaded onto the storage transmission structure.

In an embodiment, the storage detection structure further includes a second storage detection unit; the second storage detection unit is located at a lesser top layer of the consumable box storage mechanism; and the consumable box automatic transmission method further includes a step that the consumable boxes are loaded into the consumable box storage mechanism and further includes the following steps:

the storage transmission structure is controlled to rise or fall along the height direction of the consumable box storage mechanism according to a detection signal sent by the second storage detection unit;

the storage transmission structure is controlled to stop moving whenever the second storage detection unit detects one or more consumable boxes; and the storage transmission structure is controlled to move upward for one layer along the height direction of the consumable box storage mechanism whenever the second storage detection unit does not detect any consumable box.

In an embodiment, the consumable box automatic transmission method further includes a step that the consumable box storage mechanism executes a counting operation and includes the following steps:

the storage transmission structure is controlled to fall along the height direction of the consumable box storage mechanism till the storage transmission structure moves to the bottom of the consumable box storage mechanism and the storage transmission structure stops moving;

the storage transmission structure is controlled to rise along the height direction of the consumable box storage mechanism till the second storage detection unit detects the consumable box or the storage transmission structure moves to the lesser top layer of the storage transmission structure and the storage transmission structure stops moving; and the actual number of the consumable boxes in the consumable box storage mechanism under the current status is calculated according to the number of layers the storage transmission structure moves and the storage capacity of the consumable box storage mechanism.

In an embodiment, when the consumable box lifting mechanism transmits one of the consumable boxes to the top layer of the consumable box lifting mechanism, another of the consumable boxes can be loaded into the consumable box storage mechanism.

In an embodiment, the consumable box lifting mechanism includes a lifting detection structure and a lifting transmission structure configured to lift the consumable boxes; the lifting detection structure includes a first lifting detection unit; the first lifting detection unit is arranged at the top layer of the consumable box lifting mechanism, and the second lifting detection unit is arranged at a bottom of the consumable box lifting mechanism; the consumable box automatic transmission method further includes a step that the consumable box lifting mechanism executes a counting operation and includes the following steps:

the lifting transmission structure is controlled to move upward along the height direction of the consumable box lifting mechanism;

the lifting transmission structure is controlled to move downward along the height direction of the consumable box lifting mechanism if the first lifting detection unit detects one or more consumable boxes;

the lifting transmission structure is controlled to stop moving if the second lifting detection unit detects one or more consumable boxes; and the actual number of the consumable boxes in the consumable box lifting mechanism under the current status is calculated according to the number of layers the lifting transmission structure moves from the first lifting detection unit to the second lifting detection unit and the storage capacity of the consumable box lifting mechanism.

In an embodiment, the step that the consumable box lifting mechanism executes the counting operation further includes the following steps:

the first lifting detection unit does not detect any consumable box when the lifting transmission structure moves from the bottom of the consumable box lifting mechanism to the top layer;

or, the second lifting detection unit does not detect any consumable box when the lifting transmission structure moves from the top layer of the consumable box lifting mechanism to the bottom; and the number of the consumable boxes in the consumable box lifting mechanism is zero.

A chemiluminescence detector includes a sample adding device, a reaction device, a cleaning device, a luminescence detection device, a control device and a consumable box automatic transmission device as claimed in any one of the above technical characteristics.

The consumable box automatic transmission device can convey each of consumable boxes to a preset position; and the control device sequentially moves consumables in the consumable boxes to the sample adding device, the reaction device, the cleaning device and the luminescence detection device.

After adopting the above technical solutions, some embodiments achieve the following beneficial effects.

According to the chemiluminescence detector, the consumable box automatic transmission device and transmission method thereof in some embodiments, multiple consumable boxes are stored in the consumable box storage mechanism, the consumable box storage mechanism is able to drive the consumable boxes to move and transmit the consumable boxes to the consumable box lifting mechanism, and the consumable box lifting mechanism further lifts the consumable boxes to the top layer of the consumable box lifting mechanism; in this way, the effect that the consumable box storage mechanism and the consumable box lifting mechanism is able to transmit the consumable boxes in parallel can be implemented; in addition, when the consumable boxes in the consumable box storage mechanism are conveyed in part or in full to the consumable box lifting mechanism, some new consumable boxes can be loaded into the consumable box storage mechanism, with no impact on the transmission of the consumable boxes by the consumable box lifting mechanism above the consumable box storage mechanism; the problems that the safety is low and the detection efficiency is affected due to the fact that the consumables need to be added frequently can be effectively solved, and the continuous consumable box conveyance is achieved, thereby reducing manual care or frequent manual operation, improving the safety performance of consumable box conveyance, and guaranteeing the detection efficiency.

Figure 1:
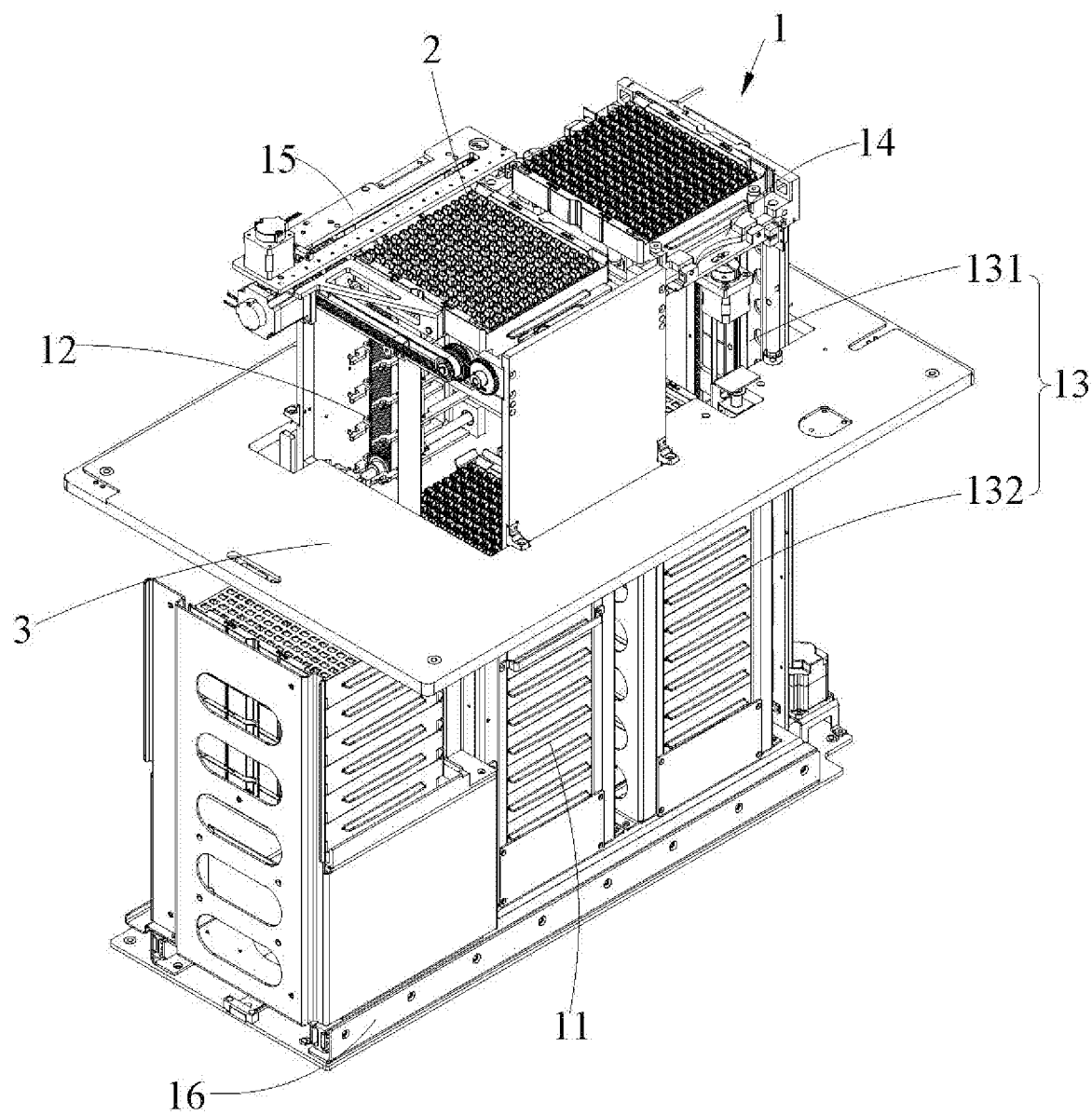
FIG. 1 is a stereogram of a consumable box automatic transmission device in an embodiment of the present disclosure from one direction.

In the drawings:
1—a consumable box automatic transmission device;
  11—a consumable box storage mechanism;
    111—a storage transmission structure;
      1111—a storage rise-fall component;
      1112—a storage support portion;
      1113—a storage guide component;
    112—a storage frame structure;
    113—a storage drive structure;
    114—a storage detection structure;
      1141—a first storage detection unit;
      1142—a second storage detection unit;
    115—a rise control button;
    116—a fall control button;
  12—a consumable box lifting mechanism;
    121—a lifting transmission structure;
      1211—a rotating component;
        12111—a rotating belt;
        12112—a rotating shaft; 121121—limiting barrier;
      1212—a rotating support portion;
    122—a lifting frame structure;
      1221—a lifting border component;
      1222—a lifting surrounding plate;
      1223—a lifting side plate;
    123—a lifting drive structure;
      1231—a lifting drive motor;
      1232—a lifting transmission component; 12321—a lifting synchronous belt; 12322—a lifting synchronous pulley; 12323—a lifting transmission gear;
      1233—a braking unit;
    124—a lifting detection structure;
      1241—a lifting locating unit;
      1242—a first lifting detection unit;
      1243—a second lifting detection unit;
  13—a consumable box recycling mechanism;
    131—a first recycling storage structure;
    132—a second recycling storage structure;
    133—a recycling transmission structure;
  14—a consumable box positioning and dropping mechanism;
  15—a push mechanism;
    151—a push mounting plate;
    152—a push drive structure;
      1521—a push gear;
      1522—a push rack;
    153—a push sliding structure;
      1531—a push slide component; 15311—a push slide rail, 15312—a push slide block; 15313—a push barrier;
      1532—a push component; 15321—a push rod portion; 15322—a push locating element;
    154—a push bottom plate;
    155—a push transmission structure;
      1551—a push transmission motor;
      1552—a push drive component;
    156—a push plate;
    157—a push initialization detection element;
  16—a drawer mechanism;
2—a consumable box;
3—a mounting platform.

DETAILED DESCRIPTION OF THE EMBODIMENTS

In order for clearer explanations of purposes, technical solutions and advantages of the present disclosure, the chemiluminescence detector, the consumable box automatic transmission device and the transmission method thereof in the present disclosure are further described in details in combination with embodiments and accompanying drawings. It should be understood that the specific examples described herein are only for the purpose of explaining the present disclosure but not for limiting the present disclosure.

Figure 2:
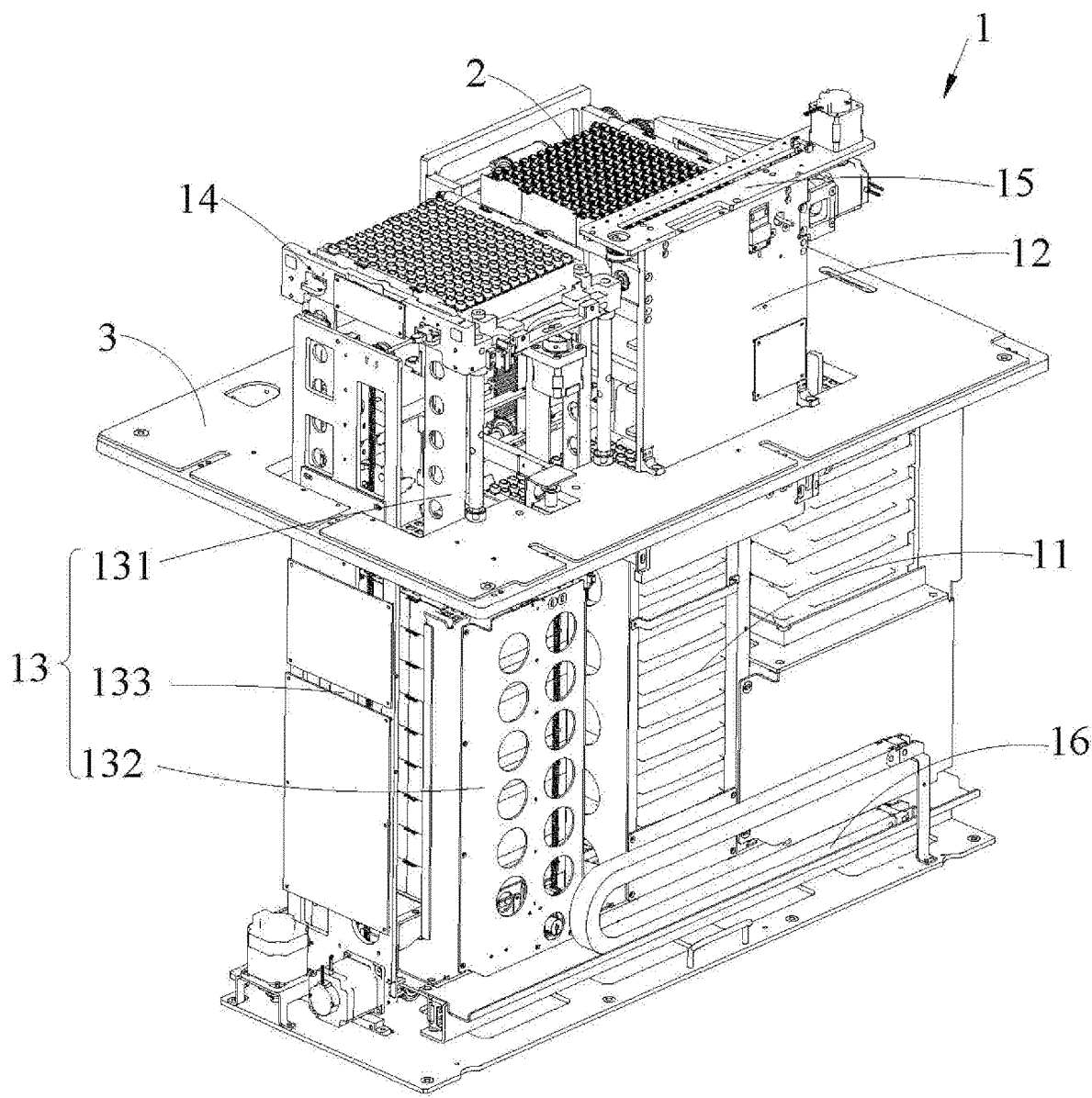
FIG. 2 is a stereogram of the consumable box automatic transmission device as shown in FIG. 1 from another direction.
Figure 3:
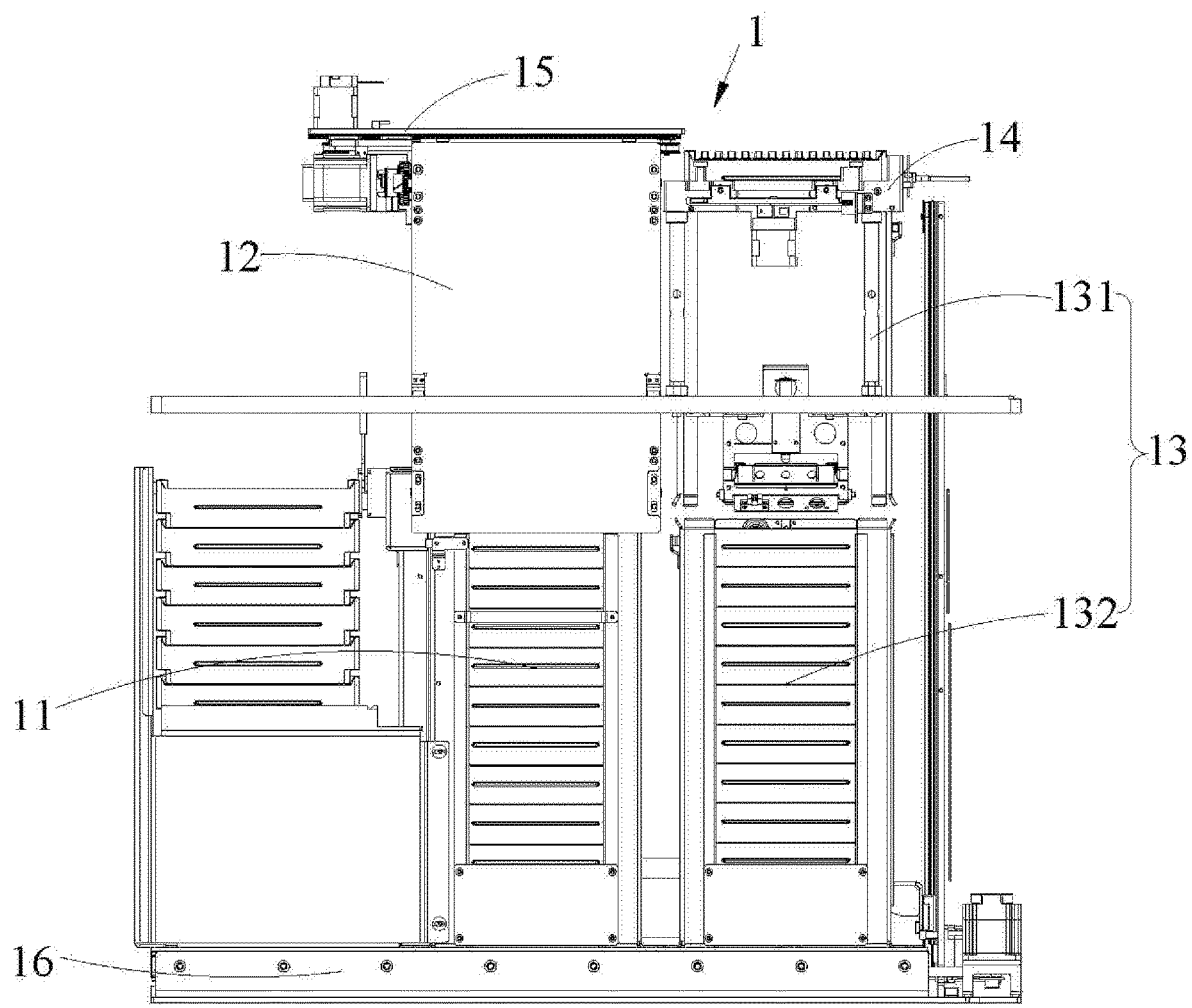
FIG. 3 is a front view of the consumable box automatic transmission device as shown in FIG. 1.
Figure 4:
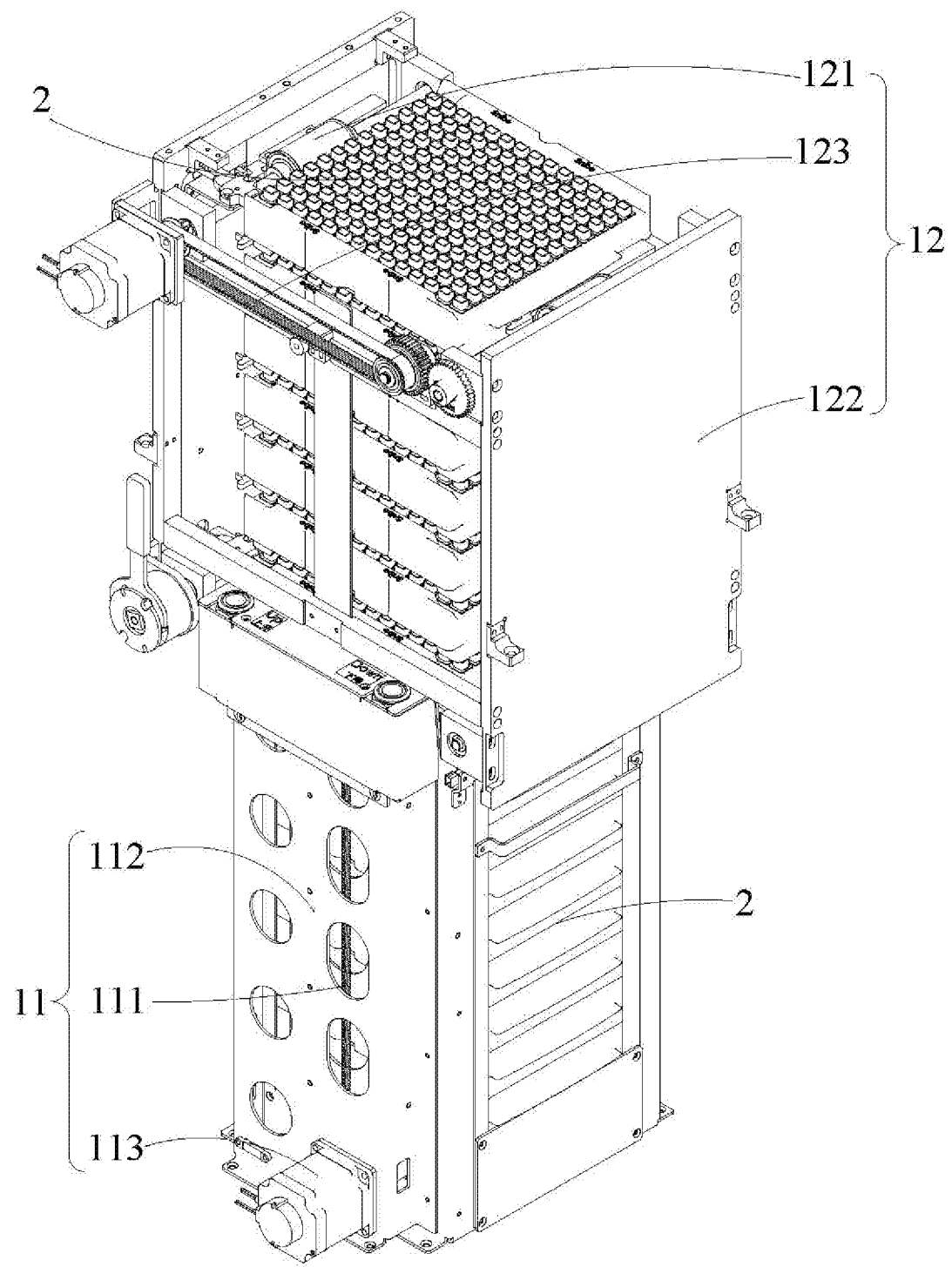
FIG. 4 is a stereogram of a consumable box storage mechanism and a consumable box lifting mechanism matching in the consumable box automatic transmission device as shown in FIG. 1.
Figure 5:
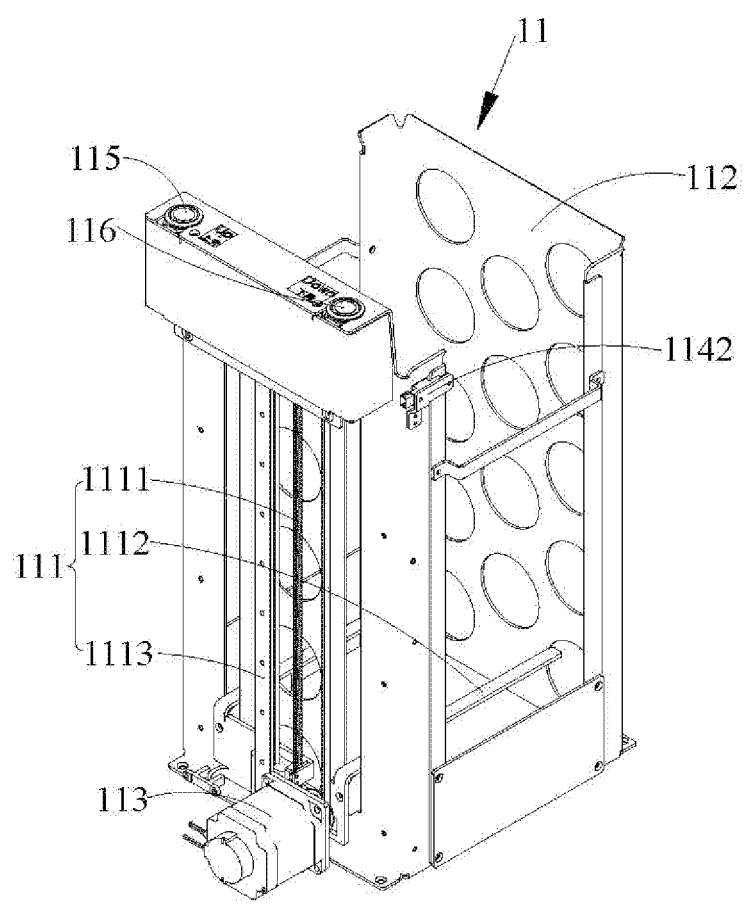
FIG. 5 is a stereogram of the consumable box storage mechanism as shown in FIG. 4.
Figure 6:
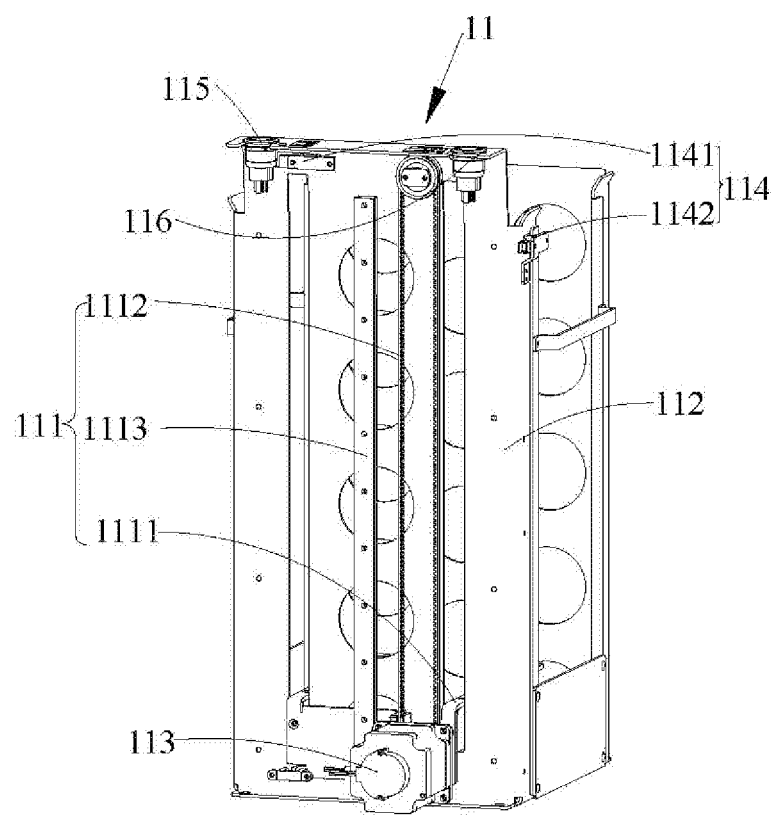
FIG. 6 is another stereogram of the consumable box storage mechanism as shown in FIG. 5.

Referring to FIG. 1 to FIG. 3, the present disclosure provides a consumable box automatic transmission device 1. The consumable box automatic transmission device 1 is applied to a chemiluminescence detector and is configured to convey and recycle a consumable box 2. A large number of consumables are stored in the consumable box 2; when the consumable box automatic transmission device 1 of an embodiment transmits the consumable box 2 to a specified position, the chemiluminescence detector grabs and uses the consumables in the consumable box 2; when the consumables in the consumable box 2 are used up, the consumable box automatic transmission device 1 can further recycle the used consumable box 2, thereby implementing automatic transmission and recycling of the consumable box 2. Through the consumable box automatic transmission device 1 of the present embodiment, the problems that the safety is low and the detection efficiency is affected due to the fact that the consumable needs to be added frequently at present can be effectively solved, and the continuous conveyance of the consumable box 2 is achieved, thereby reducing manual care or frequent manual operation, guaranteeing the safety performance of consumable box 2 conveyance, and improving the overall detection efficiency. Besides, the consumable box automatic transmission device 1 of the present disclosure can store multiple consumable boxes 2, and multiple consumable boxes 2 can be placed in a laminated manner, thereby implementing large capacity storage of the consumable boxes 2, and minimizing occupancy in the layout space of the instrument.

Referring to FIG. 1 and FIG. 4 to FIG. 6, the consumable box automatic transmission device 1 in the present embodiment includes a consumable box storage mechanism 11 and a consumable box lifting mechanism 12. The consumable box storage mechanism 11 is configured to load and store multiple consumable boxes 2; the consumable box lifting mechanism 12 is configured to store and lift the consumable boxes 2, thereby implementing conveyance of the consumable boxes 2. The consumable box lifting mechanism 12 is located above the consumable box storage mechanism 11; the consumable box lifting mechanism 12 can convey the consumable boxes 2 in the consumable box storage mechanism 11 to a top layer. The consumable box storage mechanism 11 stores multiple consumable boxes 2; when the consumable boxes 2 in the consumable box storage mechanism 11 are conveyed in part or in full to the consumable box lifting mechanism 12, some new consumable boxes 2 can be loaded into the consumable box storage mechanism 11, so that the consumable box lifting mechanism 12 lifts the consumable boxes 2 continuously, the continuous loading of the consumable boxes 2 is implemented, and overall efficiency is improved.

In addition, the consumable box storage mechanism 11 and the consumable box lifting mechanism 12 is able to respectively transmit the consumable boxes 2. The consumable box lifting mechanism 12 and the consumable box storage mechanism 11 can operate independently, and respectively transmit the consumable boxes 2 in parallel. That is to say, the consumable box storage mechanism 11 drives the consumable boxes 2 to rise or fall without affecting the operation of the consumable box lifting mechanism 12, and the consumable box lifting mechanism 12 drives the consumable boxes 2 to rise or fall without affecting the operation of the consumable box storage mechanism 11. In this way, the consumable boxes 2 can be added into the consumable box storage mechanism 11 under the consumable box automatic transmission device 1 at any time, with no impact on the conveyance of the consumable boxes 2 by the consumable box lifting mechanism 12 above the consumable box storage mechanism 11, thereby providing convenience for the continuous loading of the consumable boxes 2, and improving overall working efficiency. Meanwhile, the consumable boxes 2 can be added in time, and a shortage phenomenon can be prevented. It may be understood that, the consumable boxes 2 in the present embodiment are configured to support consumables for sample detection and analysis, such as reaction cups, test tubes, sample slides and sample tubes; when supporting the reaction cups, the consumable boxes 2 are reaction cup boxes. Besides, the shape of the consumable boxes 2 is not limited in principle, but can be square, round or any other shape, as long as the consumable boxes 2 are provided with an ear-like portion, by which the consumable box lifting mechanism 12 is able to lift the consumable boxes 2.

As an implementable embodiment, the consumable boxes 2 in the consumable box storage mechanism 11 are provided in a laminated manner; in this way, the large capacity storage of the consumable boxes 2 is implemented, the occupancy in the arrangement space of the instrument is minimized, the structure of the consumable box automatic transmission device 1 is compact, and thus the overall size of the chemiluminescence detector is reduced. The consumable box storage mechanism 11 is able to drive multiple consumable boxes 2 to move synchronously, so that the consumable boxes 2 are transmitted to the consumable box lifting mechanism 12. Multiple consumable boxes 2 are supported in a layered manner in the consumable box lifting mechanism 12; thus, the consumable box lifting mechanism 12 can store and lift the consumable boxes 2. In this way, the large capacity storage of the consumable boxes 2 is implemented, the occupancy in the arrangement space of the instrument is minimized, the structure of the consumable box automatic transmission device 1 is compact, and thus the overall size of the chemiluminescence detector is reduced.

Preferably, the consumable box lifting mechanism 12 includes a lifting transmission structure 121; the lifting transmission structure 121 can support multiple consumable boxes 2 therein in a layered manner and is able to drive multiple consumable boxes 2 to move synchronously. The consumable box storage mechanism 11 includes a storage transmission structure 111; the storage transmission structure 111 can store multiple consumable boxes 2 provided in a laminated manner, the storage transmission structure 111 can drive the multiple consumable boxes 2 to move synchronously, and the storage transmission structure 111 can be able to transmit the multiple consumable boxes 2 to the lifting transmission structure 121 one by one. The lifting transmission structure 121 can implement layered support and transmission of the consumable boxes 2, which means that a distance exists between two adjacent consumable boxes 2 in the lifting transmission structure 121. Besides, the consumable boxes 2 in the storage transmission structure 111 can be provided in a laminated manner; that is to say, two adjacent consumable boxes 2 are in mutual contact without any gap; and thus, the storage capacity of the consumable boxes 2 can be improved.

Of course, in other embodiments of the present disclosure, the specific structure of the storage transmission structure 111 is the same as that of the lifting transmission structure 121; that is to say, the storage transmission structure 111 also supports and stores the consumable boxes 2 in a layered manner; and the storage transmission structure 111 and the lifting transmission structure 121 are provided in a staggered manner, thereby providing convenience for transmitting the consumable boxes 2 on the consumable box storage mechanism 111 to the consumable box lifting mechanism 12.

Referring to FIG. 5 to FIG. 10, it may be understood that, the consumable box storage mechanism 11 has a storage capacity; when the number of the consumable boxes 2 in the consumable box storage mechanism 11 is larger than the storage capacity, the highest one of the consumable boxes 2 in the consumable box storage mechanism 11 interferes with the consumable box lifting mechanism 12 or other structures of the chemiluminescence detector, thereby affecting the use; therefore, the number of the consumable boxes 2 in the consumable box storage mechanism 11 may not exceed the storage capacity. Preferably, in this embodiment, when the consumable box storage mechanism 11 is fully occupied by the consumable boxes 2, no consumable box 2 is at the top layer of the consumable box storage mechanism 11; that is to say, the consumable boxes 2 in the consumable box storage mechanism 11 are stored in a space from the bottom of the consumable box storage mechanism 11 to a layer below the top layer of the consumable box storage mechanism 11, namely a lesser top layer. It is to be noted that, a transmission position is above the consumable box storage mechanism 11; the consumable box storage mechanism 11 is able to transmit upward the consumable box 2 to the transmission position, and the consumable box lifting mechanism 12 can receive the consumable box 2 transmitted by the consumable box storage mechanism 11 at the transmission position. That is to say, the transmission position is higher than the position of a lesser top layer of the consumable box storage mechanism 11, and is lower than a position where the consumable box lifting mechanism 12 finishes receiving the consumable box 2.

The consumable box lifting mechanism 12 also has a storage capacity; the storage capacity is the maximum number of the consumable boxes 2 that can be stored between the bottom of the consumable box lifting mechanism 12 and the lesser top layer of the consumable box lifting mechanism 12. When the consumable box lifting mechanism 12 is full of the consumable boxes 2, no consumable box 2 is at the top layer of the consumable box lifting mechanism 12; the highest one of the consumable boxes 2 in the consumable box lifting mechanism 12 is at the lesser top layer. When the consumable box automatic transmission device 1 needs to transmit each of the consumable boxes 2 to a preset position (where the chemiluminescence detector grabs the consumables in the consumable box 2), the consumable box lifting mechanism 12 lifts the consumable boxes 2 as a whole, so that the highest one of the consumable boxes 2 in the consumable box lifting mechanism 12 is lifted from the lesser top layer to the top layer, the lowest one of the consumable boxes 2 is risen for one layer from the bottom, and the bottom of the consumable box lifting mechanism 12 is vacated. The consumable box automatic transmission device 1 forwards each of the consumable boxes 2 at the top layer of the consumable box lifting mechanism 12 to the preset position, and the chemiluminescence detector grabs the consumables in the consumable boxes 2 at the preset position. Again, when each of the consumable boxes 2 needs to be conveyed to the preset position, the consumable box lifting mechanism 12 lifts the consumable boxes 2 as a whole, so that the consumable boxes 2 are moved from the lesser top layer to the top layer; through such repeated operation, the consumable boxes 2 are lifted.

During transmission, the consumable box storage mechanism 11 drives the consumable boxes 2 to rise to the transmission position; the consumable box lifting mechanism 12 receives the consumable boxes 2 at the transmission position, and gradually lifts the consumable boxes 2. It may be understood that, the transmission position is higher than the lesser top layer of the consumable box storage mechanism 11, thereby providing convenience for the consumable box lifting mechanism 12 to receive the consumable boxes 2 conveyed by the consumable box storage mechanism 11, guaranteeing the receiving reliability, and thus guaranteeing the overall operational reliability. Preferably, the transmission position is located in the top layer area of the consumable box storage mechanism 11; the consumable box storage mechanism 11 lifts the highest one of the consumable boxes 2 to the transmission position in the top layer area; the consumable box lifting mechanism 12 receives the consumable box 2 at the transmission position; thus, the rising distance of the consumable box storage mechanism 11 can be reduced, the space occupied by the consumable box storage mechanism 11 and the consumable box lifting mechanism 12 is reduced, and thus the overall size is reduced. The transmission position is a middle position at the top layer of the consumable box storage mechanism 11; thus, when the consumable box storage mechanism 11 moves upward for a preset distance, the highest one of the consumable boxes 2 is at the transmission position, thereby providing convenience for the consumable box lifting mechanism 12 to receive the consumable boxes 2. In this embodiment, the preset distance is a height of a half layer the consumable boxes 2 move.

As shown in FIG. 5 to FIG. 10, when the consumable box automatic transmission device 1 of the present embodiment transmits the consumable boxes 2, the consumable box storage mechanism 11 transmits the highest one of the consumable boxes 2 therein upward, so that the highest one of the consumable boxes 2 in the consumable box storage mechanism 11 is located at the transmission position, and the consumable box lifting mechanism 12 receives the consumable box 2 at the transmission position; after reception, the consumable box lifting mechanism 12 moves upward, the consumable box storage mechanism 11 moves upward and transmits another consumable box 2 to the transmission position, and the consumable box lifting mechanism 12 again receives the consumable box 2 at the transmission position; through such repeated operation, the consumable box lifting mechanism 12 gradually rises and receives the consumable boxes 2; the consumable box lifting mechanism 12 stops moving upward when the highest one of the consumable boxes 2 in the consumable box lifting mechanism 12 is moved to the lesser top layer of the consumable box lifting mechanism 12. When transmitting the consumable box 2 to the preset position, the consumable box lifting mechanism 12 moves upward for one layer, and lifts a consumable box 2 at the lesser top layer to the top layer of the consumable box lifting mechanism 12; the consumable box automatic transmission device 1 conveys the consumable box 2 at the top layer of the consumable box lifting mechanism 12 to the preset position; the chemiluminescence detector grabs the consumables in the consumable box 2 at the preset position. When needing to convey the consumable box 2 to the preset position again, the consumable box lifting mechanism 12 moves upward for one layer, and lifts a consumable box 2 at the lesser top layer to the top layer of the consumable box lifting mechanism 12; through such repetition, when the consumable boxes 2 in the consumable box lifting mechanism 12 are used up or have a small amount, the consumable box lifting mechanism 12 loads other consumable boxes 2 again.

It may be understood that, when the consumable boxes 2 in the consumable box lifting mechanism 12 are conveyed in full or at least in part, the consumable box lifting mechanism 12 receives the consumable boxes 2 transmitted by the consumable box storage mechanism 11. Thus, automatic and continuous conveyance of the consumable boxes 2 can be implemented, and the overall operational efficiency is improved. In one case, new consumable boxes 2 need to be loaded when the consumable boxes 2 in the consumable box lifting mechanism 12 are used up or no consumable box 2 exists in the consumable box lifting mechanism 12. Specifically, the consumable box storage mechanism 11 transmits one consumable box 2 to the transmission position, and the consumable box lifting mechanism 12 receives the consumable box 2 at the transmission position; after reception, the consumable box lifting mechanism 12 moves upward, the consumable box storage mechanism 11 moves upward and transmits another consumable box 2 to the transmission position, and the consumable box lifting mechanism 12 again receives the consumable box 2 at the transmission position; through such repeated operation, the consumable box lifting mechanism 12 gradually rises and receives the consumable boxes 2; the consumable box lifting mechanism 12 stops moving upward when the highest one of the consumable boxes 2 in the consumable box lifting mechanism 12 is moved to the lesser top layer of the consumable box lifting mechanism 12, which indicates that the consumable box lifting mechanism 12 finishes loading. In another case, when at least a part of the consumable boxes 2 in the consumable box lifting mechanism 12 are conveyed or a part of the consumable boxes 2 in the consumable box lifting mechanism 12 are left, the consumable box lifting mechanism 12 makes the left consumable boxes 2 therein to fall, so that the lowest one of the consumable boxes 2 in the consumable box lifting mechanism 12 is located above the transmission position; then the consumable box storage mechanism 11 transmits one consumable box 2 to the transmission position, and the consumable box lifting mechanism 12 receives the consumable box 2 at the transmission position; after reception, the consumable box lifting mechanism 12 moves upward, the consumable box storage mechanism 11 moves upward and transmits another consumable box 2 to the transmission position, and the consumable box lifting mechanism 12 again receives the consumable boxes 2 at the transmission position; through such repeated operation, the consumable box lifting mechanism 12 gradually rises and receives the consumable boxes 2; the consumable box lifting mechanism 12 stops moving upward when the highest one of the consumable boxes 2 in the consumable box lifting mechanism 12 is moved to the lesser top layer of the consumable box lifting mechanism 12, which indicates that the consumable box lifting mechanism 12 finishes loading; in this way, no vacancy occurs between the newly loaded consumable boxes 2 and the consumable boxes 2 left in the consumable box lifting mechanism 12, and the consumable box lifting mechanism 12 can continuously convey the consumable boxes 2, thereby guaranteeing operational performance.

Of course, in another embodiment of the present disclosure, the consumable box lifting mechanism 12 can also adopt the transmission mode of conveying a consumable box 2 and then loading a consumable box 2. Specifically, when the consumable boxes 2 at the lesser top layer of the consumable box lifting mechanism 12 are lifted to the top layer, a vacancy occurs at a bottom of the consumable box lifting mechanism 12; then, the consumable box storage mechanism 11 transmits the consumable boxes 2 upward, and lifts one consumable box 2 to the vacancy of the consumable box lifting mechanism 12, and the consumable box 2 is at the transmission, position of the consumable box storage mechanism 11; then when the consumable box lifting mechanism 12 moves a consumable box 2 at the lesser top layer to the top layer, the consumable box lifting mechanism 12 receives the consumable box 2 at the transmission position and moves upward. When needing to again lift one consumable box 2 to the top layer of the consumable box lifting mechanism 12, the consumable box storage mechanism 11 conveys the highest one of the consumable boxes 2 therein to the transmission position, and the consumable box lifting mechanism 12 again receives the consumable box 2 at the transmission position; through such repetition, automatic and continuous conveyance of the consumable boxes 2 is implemented.

In addition, the consumable box storage mechanism 11 can be movably abutted with or separated from the consumable box lifting mechanism 12. When the consumable box storage mechanism 11 is abutted with the consumable box lifting mechanism 12, the consumable box storage mechanism 11 transmits the consumable boxes 2 to the consumable box lifting mechanism 12, and the consumable box lifting mechanism 12 lifts the consumable boxes 2 to the top layer of the consumable box lifting mechanism 12. When the consumable box storage mechanism 11 is separated from the consumable box lifting mechanism 12, a user can load new consumable boxes 2 into the consumable box storage mechanism 11, thereby implementing continuous loading of the consumable boxes 2. The consumable box lifting mechanism 12 lifts the consumable boxes 2 through a rise-fall manner; the consumable box storage mechanism 11 conveys the consumable boxes 2 to the transmission position; the consumable box lifting mechanism 12 receives the consumable boxes 2 at the transmission position, and lifts the consumable boxes 2 to the lesser top layer of the consumable box lifting mechanism 12. When in operation, the consumable box lifting mechanism 12 lifts the consumable boxes 2 from the lesser top layer to the top layer, thereby providing convenience for conveying the consumable boxes 2 to the preset position. It is to be noted that the preset position refers to a position where the chemiluminescence detector grabs the consumables, such as reaction cups in the consumable boxes 2.

It is further to be noted that, the consumable box storage mechanism 11 is also provided with a loading position; the loading position is a position at the top layer of the consumable box storage mechanism 11; that is to say, the consumable box storage mechanism 11 loads the consumable boxes 2 at the top layer. If no consumable box 2 is in the consumable box storage mechanism 11 when the consumable box storage mechanism 11 is separated from the consumable box lifting mechanism 12, the consumable box storage mechanism 11 can be directly separated from the consumable box lifting mechanism 12; if a consumable box 2 is in the consumable box storage mechanism 11, the consumable box storage mechanism 11 needs to make the highest one of the consumable boxes 2 therein falls to a position below the loading position, so that the consumable box storage mechanism 11 can be smoothly separated from the consumable box lifting mechanism 12. Generally, the consumable boxes 2 are located at a bottom of the consumable box storage mechanism 11; when the consumable boxes 2 need to be transmitted, the consumable box storage mechanism 11 transmits the consumable boxes 2 upward, thereby preventing one of the consumable boxes 2 at the transmission position from interfering with the chemiluminescence detector when the consumable box storage mechanism 11 is separated from the consumable box lifting mechanism 12, and affecting operational reliability. In addition, the consumable box storage mechanism 11 loads the consumable boxes 2 at the loading position; when the loading is finished, the highest one of the consumable boxes 2 in the consumable box storage mechanism 11 fall below the loading position, thereby preventing the highest one of the consumable boxes 2 in the consumable box storage mechanism 11 from touching the consumable box lifting mechanism 12 when the consumable box storage mechanism 11 is abutted with the consumable box lifting mechanism 12.

Referring to FIG. 1 and FIG. 4 to FIG. 6, further, the consumable box storage mechanism 11 includes a storage frame structure 112 and a storage drive structure 113; the storage drive structure 113 is provided on the storage frame structure 112; the storage transmission structure 111 is provided in the storage frame structure 112 in a rise-fall manner; the storage drive structure 113 is in transmission connection with the storage transmission structure 111. The storage drive structure 113 drives the storage transmission structure 111, thereby driving multiple consumable boxes 2 to rise or fall in the storage frame structure 112. The storage frame structure 112 is configured to store and support the storage transmission structure 111, so that the storage transmission structure 111 can move in the storage frame structure 112 and transmit the consumable boxes 2. The storage drive structure 113 serves as a power source of the storage transmission structure 111 and drives the storage transmission structure 111 to rise or fall, thereby driving the consumable boxes 2 to rise or fall.

Optionally, the storage frame structure 112 includes multiple storage surrounding plates; the multiple storage surrounding plates surround to form a storage space; the storage transmission structure 111 is provided in the storage space; the multiple consumable boxes 2 are located in the storage space. The storage drive structure 113 is provided on the storage surrounding plates. In addition, the storage frame structure 112 is provided with a storage opening; the storage opening is disposed along the height direction; in this way, it is convenient to observe the number of the consumable boxes 2 in the storage space and count the number of the consumable boxes 2, and the user can know the number of the consumable boxes 2 in the consumable box storage mechanism 11 and load consumable boxes 2 into the storage space in time, thereby guaranteeing continuous loading of the consumable boxes 2.

Optionally, the storage drive structure 113 includes a storage drive motor and a storage output component; the storage drive motor is fixed on the storage frame structure 112, and the storage output component is in transmission connection with the storage transmission structure 111, so that the power of the storage drive motor is transmitted to the storage transmission structure 111. The storage output component can be a coupling or a speed reducer or any other component that is able to transmit movement.

The storage transmission structure 111 includes a storage support plate, a storage rise-fall component 1111 and a storage support portion 1112 provided on the storage rise-fall component 1111; the storage rise-fall component 1111 is movably provided on the storage support plate, and is connected with the storage output component. The storage support plate is provided on the storage surrounding plate; the storage support portion 1112 can support multiple consumable boxes 2 that are provided in a laminated manner; the storage drive motor is able to drive the storage rise-fall component 1111 through the storage output component to drive the storage support portion 1112 to rise or fall. The storage output component is in transmission connection with the storage rise-fall component 1111; the storage drive motor drives the storage output component to move; the storage output component is able to drive the storage rise-fall component 1111 to rise or fall, so that the storage rise-fall component 1111 drives the storage support portion 1112 thereon to move; accordingly, the storage support portion 1112 drives multiple consumable boxes 2 thereon to rise or fall together, and the consumable boxes 2 are conveyed to the bottom of the lifting transmission structure 121. Of course, the storage support plate and the storage surrounding plates can also be integrated; that is to say, the storage rise-fall component 1111 is provided on the storage surrounding plates.

The storage rise-fall component 1111 may be a synchronous belt transmission component, a chain transmission component, a gear transmission component, a screw transmission component or any other structure that can implement rise and fall. In this embodiment, the storage rise-fall component 1111 can be a synchronous belt transmission component, including two storage synchronous pulleys and a storage synchronous belt; the two storage synchronous pulleys are arranged along a height direction; one storage synchronous pulley is rotatably located at the top of the storage support plate; the other synchronous pulley is rotatably located at a bottom of the storage support plate; the storage synchronous belt is provided on the two storage synchronous pulleys in a sleeving manner. An output end of the storage drive motor is connected with one storage synchronous pulley through the storage output component, so as to drive the storage synchronous pulley to move; thus, the storage synchronous pulley drives the storage synchronous belt to move. The storage support portion 1112 is provided on the storage synchronous belt; the storage synchronous belt drives the storage support portion 1112 to rise or fall together, thereby driving the consumable boxes 2 to rise or fall together. Of course, in other embodiments of the present disclosure, the combination of the storage drive structure 113 and the storage transmission component can also be a drive structure that can implement rise and fall, such as a cylinder and an electromagnet. Of course, in other embodiments of the present disclosure, the storage drive motor can also be in direct transmission connection with the storage rise-fall component 1111. Optionally, the storage synchronous pulleys and the storage synchronous belt are provided with tooth portions that are engaged mutually, thereby guaranteeing reliable transmission between the storage synchronous pulleys and the storage synchronous belt, and preventing slipping.

Optionally, the storage support portion 1112 is arranged by stretching out of the storage support plate, so as to place multiple consumable boxes 2. The storage synchronous belt can move to drive the storage support portion 1112 to rise or fall, so that the storage support portion 1112 drives multiple consumable boxes 2 to rise or fall synchronously. Preferably, the storage support portion 1112 is a support plate, a pull bar or a clamping jaw, a lug boss or a suspension plate that can support the consumable boxes 2.

Optionally, the storage transmission structure 111 further includes a storage guide component 1113; the storage guide component 1113 is provided on the storage support plate, and is connected with the storage support portion 1112; thus, the storage guide component 1113 guides the storage support portion 1112 to rise or fall, preventing the storage support portion 1112 from rising and falling with deflection, and guaranteeing reliable transmission of the consumable boxes 2. Optionally, the storage guide component 1113 includes a storage guide slide rail and a storage guide slide block that can be slidably provided on the storage guide slide rail; the storage guide slide rail is provided on the storage support plate along the rise-fall direction; the storage guide slide block is fixed on the storage support portion 1112. The storage drive motor drives the storage synchronous belt to move, and the storage synchronous belt drives the storage support portion 1112 thereon to rise or fall; meanwhile, the storage support portion 1112 drives the storage guide slide block thereon to rise or fall along the storage guide slide rail, thereby driving multiple consumable boxes 2 to rise or fall. Of course, in other embodiments of the present disclosure, the storage guide component 1113 can also adopt a guide shaft and a guide hole that are matched with each other to provide a guide function, or any other structure that can provide a guide function.

Further, the consumable box storage mechanism 11 further includes a storage detection structure 114; the storage detection structure 114 is provided in the storage frame structure 112. The storage detection structure 114 is configured to detect whether a consumable box 2 is in a corresponding detection area. Further, the storage detection structure 114 includes a first storage detection unit 1141; a detection area of the first storage detection unit 1141 is located at the top layer of the storage frame structure 112; the first storage detection unit 1141 can detect whether the consumable box 2 is in the detection area. The first storage detection unit is configured to detect whether a consumable box 2 is at the top layer of the storage frame structure 112. It may be understood that, the detection area of the first storage detection unit 1141 is provided in correspondence with the loading position of the consumable box storage mechanism 11, so as to detect whether a consumable box 2 is at the loading position. In this way, when a consumable box 2 is loaded into the consumable box storage mechanism 11, the consumable box 2 is located at a top layer of the storage frame structure 112; then, the first detection unit detects the consumable box 2; the storage transmission structure 111 automatically falls for one layer and spares the top layer for an operator for continuous loading. Thus, when the consumable box storage mechanism 11 loads the consumable box 2 at the top layer, the operator can always maintain a proper posture to load the consumable box 2 without squatting, thereby saving energy and operating conveniently. Besides, the first storage detection unit 1141 can further ensure that no consumable box 2 is at the top layer of the consumable box storage mechanism 11. When the consumable box storage mechanism 11 is full of the consumable boxes 2, the first storage detection unit 1141 can further detect whether a consumable box 2 is at the top layer of the consumable box storage mechanism 11, thereby preventing the top layer of the consumable box storage mechanism 11 with the consumable box 2 from touching and interfering with other structures of the chemiluminescence detector. Preferably, the first storage detection unit 1141 is a first storage sensor; the first storage sensor is arranged at the top layer of the storage frame structure 112; the detection area of the first storage sensor is correspondingly located at the top layer of the storage frame structure 112, so as to detect whether a consumable box 2 exists. Of course, in other embodiments of the present disclosure, the first storage detection unit 1141 can also be any other structure that can detect whether a consumable box 2 exists.

Further, the storage detection structure 114 further includes a second storage detection unit 1142; the second storage detection unit 1142 is provided on the storage frame structure 112; a detection area of the second storage detection unit 1142 is located under the detection area of the first storage detection unit 1141. A movement distance that the consumable box 2 moves from the detection area of the second storage detection unit 1142 to the detection area of the first storage detection unit 1141 is a height of one consumable box 2. In other words, the detection area of the second storage detection unit 1142 is located at the lesser top layer of the storage frame structure 112; the storage transmission structure 111 drives the consumable box 2 to rise for one layer; the consumable box 2 moves from the detection area of the second storage detection unit 1142 to the detection area of the first storage detection unit 1141. That is to say, the second storage detection unit 1142 is configured to detect whether a consumable box 2 is at the lesser top layer of the storage frame structure 112. If the operator activates the first storage detection unit 1141 by mistake and the storage transmission structure 111 automatically falls for one layer, the second storage detection unit 1142 can not detect any consumable box 2 in the detection area; then the storage transmission structure 111 automatically rises for one layer. Thus, the storage transmission structure 111 can always stay at a proper height, thereby providing convenience for the operator to load a consumable box 2. Of course, in other embodiments of the present disclosure, a movement distance that the consumable box 2 moves from the detection area of the second storage detection unit 1142 to the detection area of the first storage detection unit 1141 is less than or equal to the total height of two consumable boxes 2; at this moment, two consumable boxes 2 are loaded into the consumable box storage mechanism 11, so that the highest one of the consumable boxes 2 in the consumable box storage mechanism 11 always stays at a proper height.

Additionally, the second storage detection unit 1142 can further be configured to count the number of the consumable boxes 2 in the consumable box storage mechanism 11. Specifically, when the number of the consumable boxes 2 in the consumable box storage mechanism 11 needs to be counted, the storage rise-fall component 1111 of the storage transmission structure 111 is able to drive the storage support portion 1112 to fall to the bottom of the storage frame structure 112; then the storage rise-fall component 1111 again drives the storage support portion 1112 to move upward; the storage rise-fall component 1111 stops moving upward when the second storage detection unit 1142 detects the consumable boxes 2 on the storage support portion 1112 or the storage rise-fall component 1111 moves to the lesser top layer of the consumable box storage mechanism 11. Then, according to the number of layers that the storage support portion 1112 moves upward and the storage capacity of the consumable boxes 2 stored in the storage frame structure 112 of the consumable box storage mechanism 2, the actual number of the consumable boxes 2 in the storage frame structure 112 under current status is calculated. It is to be noted that if the second storage detection unit 1142 does not detect any consumable box 2 when the storage rise-fall component 1111 moves to the lesser top layer of the consumable box storage mechanism 11, no consumable box 2 is in the consumable box storage mechanism 11, and the number of the consumable boxes 2 in the consumable box storage mechanism 11 is zero. Optionally, the number of the layers that the storage transmission mechanism 111 moves or the step number that the storage drive motor moves can be calculated through a counter or a counting module, and the like, thereby counting the number of the consumable boxes 2 in the consumable box storage mechanism 11.

It is to be noted that two situations occur when the consumable box storage mechanism 11 loads a new consumable box 2; in one situation, one or more consumable boxes 2 are left in the consumable box storage mechanism 11; in the other situation, no consumable box 2 is left in the consumable box storage mechanism 11; the following will respectively describe how the first storage detection unit 1141 and the second storage detection unit 1142 move in the two situations. When one or more consumable boxes 2 are left in the consumable box storage mechanism 11, the storage transmission structure 111 drives one or more consumable boxes 2 to rise; when the second storage detection unit 1142 detects any one of the consumable boxes 2, the storage transmission structure 111 stops moving; then, the highest one of the consumable boxes 2 on the storage transmission structure 111 is located at the lesser top layer; when the user loads a new consumable box 2 to the top layer of the consumable box storage mechanism 11 that is a loading position, the storage transmission structure 111 automatically falls for one layer, so that the highest one of the consumable boxes 2 on the storage transmission structure 111 is located at the lesser top layer of the consumable box storage mechanism 11; then no consumable box 2 is at the loading position, and the user can continue to load a new consumable box 2; through such repetition, when the consumable box storage mechanism 11 is full of the consumable boxes 2 or is filled with a needed capacity of the consumable boxes 2, the storage transmission structure 111 stops falling, and the loading of the consumable boxes 2 to the consumable box storage mechanism 11 is finished.

When no consumable box 2 is left in the consumable box storage mechanism 11, the storage transmission structure 111 rises; as the second storage unit does not detect any consumable box 2, the storage transmission structure 111 rises to the top layer of the consumable box storage mechanism 11 which is a loading position; the user loads a new consumable box 2 to the top layer of the consumable box storage mechanism 11 which is a loading position; then the storage transmission structure 111 automatically falls for one layer, so that the highest one of the consumable boxes 2 on the storage transmission structure 111 is located at the lesser top layer of the consumable box storage mechanism 11; then, no consumable box 2 is at the loading position, and the user can continue to load a new consumable box 2; through such repetition, when the consumable box storage mechanism 11 is full of the consumable boxes 2 or is filled with a needed capacity of the consumable boxes 2, the storage transmission structure 111 stops falling, and the loading of the consumable boxes 2 to the consumable box storage mechanism 11 is finished.

Optionally, the first storage detection unit 1141 and the second storage detection unit 1142 are arranged at different sides; that is to say, the first storage detection unit 1141 and the second storage detection unit 1142 are arranged at different surfaces of the storage frame structure 112, thereby preventing detection signals of the first storage detection unit 1141 and the second storage detection unit 1142 from interfering with each other, and guaranteeing the reliable operation of the storage transmission structure 111; meanwhile, the operator can avoid touching the first storage detection unit 1141 and the second storage detection unit 1142 at the same time, and prevent false operation as a result of no-load fall of the storage support portion 1112, guaranteeing accurate and reliable operation.

As an implementable embodiment, the consumable box storage mechanism 11 further includes a master control button, a rise control button 115 and a fall control button 116; the master control button, the rise control button 115 and the fall control button 116 all are provided on the storage frame structure 112; the rise control button 115 and the fall control button 116 are respectively and electrically connected with the storage transmission structure 111. When the consumable box storage mechanism 11 loads a consumable box 2, the storage transmission structure 111 has a manual mode and an automatic mode; when the storage transmission structure 111 is in the manual mode, the rise control button 115 controls the storage transmission structure 111 to rise, and the fall control button 116 controls the storage transmission structure 111 to fall; when the storage transmission structure 111 is in the automatic mode, the storage transmission structure 111 automatically rises and falls, so that the storage transmission structure 111 loads the consumable box 2 at the loading position. Besides, the rise control button 115 and the fall control button 116 can further switch the storage transmission structure 111 between the manual mode and the automatic mode. During switching, by long pressing the rise control button 115, the storage transmission structure 111 switches from the automatic mode to the manual mode, the rise control button 115 controls the storage transmission structure 111 to rise, and the fall control button 116 controls the storage transmission structure 111 to fall; by long pressing the fall control button 116, the storage transmission structure 111 switches from the manual mode to the automatic mode and the chemiluminescence detector automatically controls the storage transmission structure 111 to rise or fall. It may be understood that, long pressing means pressing for 2 s to 5 s, and controlling the storage transmission structure 111 to rise or fall means short pressing for less than 2 s.

It is to be noted that, when the storage transmission structure 111 is in the automatic mode, the rise and fall of the storage transmission structure 111 are implemented through the cooperation of the first storage detection unit 1141 and the second storage detection unit 1142. During loading, when the first storage detection unit 1141 detects a consumable box 2, the storage transmission structure 111 automatically falls for one layer; when the second storage detection unit 1142 does not detect any consumable box 2, the storage transmission structure 111 automatically rises for one layer. In the manual mode, when the rise control button 15 is pressed, the storage transmission structure 111 rises for the height of one consumable box 2; when the fall control button 116 is pressed, the storage transmission structure 111 falls for the height of one consumable box 2. In addition, when the storage transmission structure 111 does not rise according to a preset track, the rise control button 115 and the fall control button 116 can control the storage transmission structure 111 to move to the needed position. The master control button can be configured for error report and on-off control of the entire equipment.

Referring to FIG. 1 and FIG. 7 to FIG. 10, as an implementable embodiment, the consumable box lifting mechanism 12 includes a lifting frame structure 122 and a lifting drive structure 123; the lifting drive structure 123 is provided on the lifting frame structure 122; the lifting drive structure 123 is in transmission connection with the lifting transmission structure 121; the lifting transmission structure 121 is provided in the lifting frame structure 122 in a rise-fall manner. The lifting drive structure 123 drives the lifting transmission structure 121 to rise or fall in the lifting frame structure 122; the storage transmission structure 111 drives multiple consumable boxes 2 to rise; when the highest one of the consumable boxes 2 is located at a transmission position, the lifting transmission structure 121 receives the consumable box 2 at the transmission position; the lifting transmission structure 121 rises, and the storage transmission structure 111 continuously rises for one layer and transmits a consumable box 2 at the lesser top layer to the transmission position; the lifting transmission structure 121 again receives the consumable box 2 at the transmission position; when the highest one of the consumable boxes 2 on the lifting transmission structure 121 are moved to the lesser top layer of the lifting frame structure 122, the storage transmission structure 111 stops moving upward, thereby transmitting the consumable boxes 2 from the consumable box storage mechanism 11 to the consumable box lifting mechanism 12.

The lifting frame structure 122 is configured to store the consumable boxes 2, and support the lifting transmission structure 121, so that the lifting transmission structure 121 can move in the lifting frame structure 122 and transmit the consumable boxes 2. The lifting drive structure 123 is in transmission connection with the lifting transmission structure 121; the lifting drive structure 123 serves as a power source of the lifting transmission structure 121 and drives the lifting transmission structure 121 to rise or fall, thereby driving the consumable boxes 2 to rise or fall. It is to be noted that the lifting transmission structure 121 is able to transmit the consumable boxes 2 layer by layer; when a consumable box 2 at the top layer of the lifting transmission structure 121 are conveyed, the lifting transmission structure 121 is able to lift a consumable box 2 at the lesser top layer to the top layer, thereby implementing continuous conveyance and loading of the consumable boxes 2.

Figure 7:
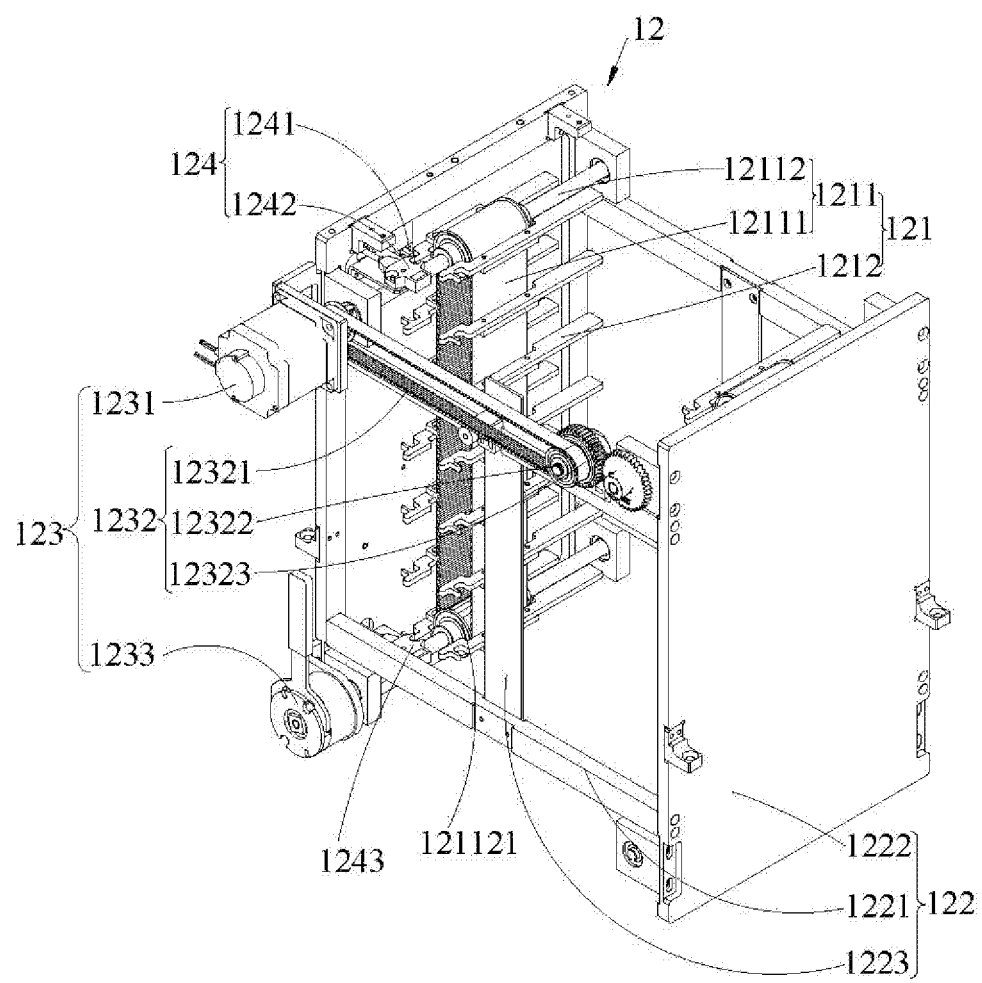
FIG. 7 is a stereogram of an embodiment of a consumable box lifting mechanism in the consumable box automatic transmission device as shown in FIG. 4.
Figure 8:
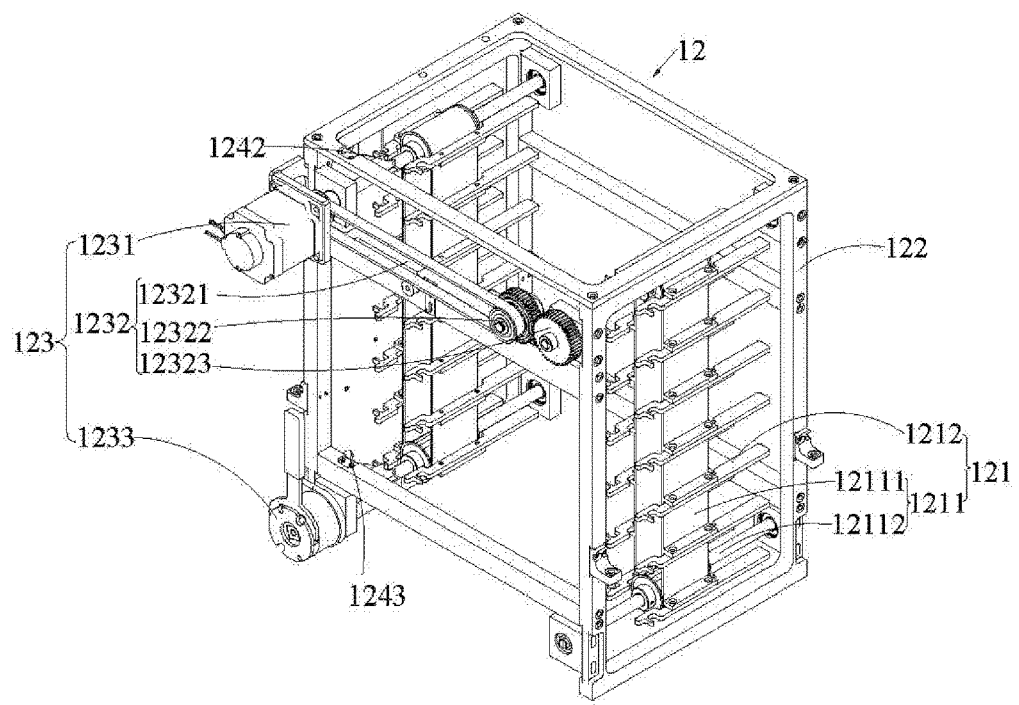
FIG. 8 is a stereogram of another embodiment of a consumable box lifting mechanism in the consumable box automatic transmission device as shown in FIG. 4.
Figure 9:
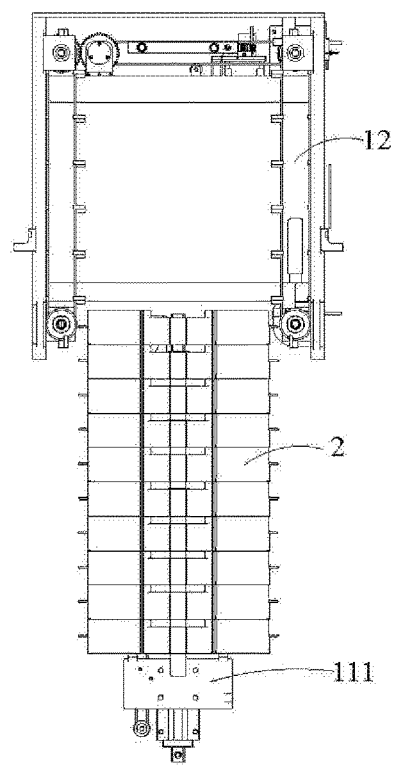
FIG. 9 is a structural schematic diagram that a storage transmission structure in the consumable box storage mechanism as shown in FIG. 4 transmits a consumable box to a consumable box lifting mechanism.
Figure 10:
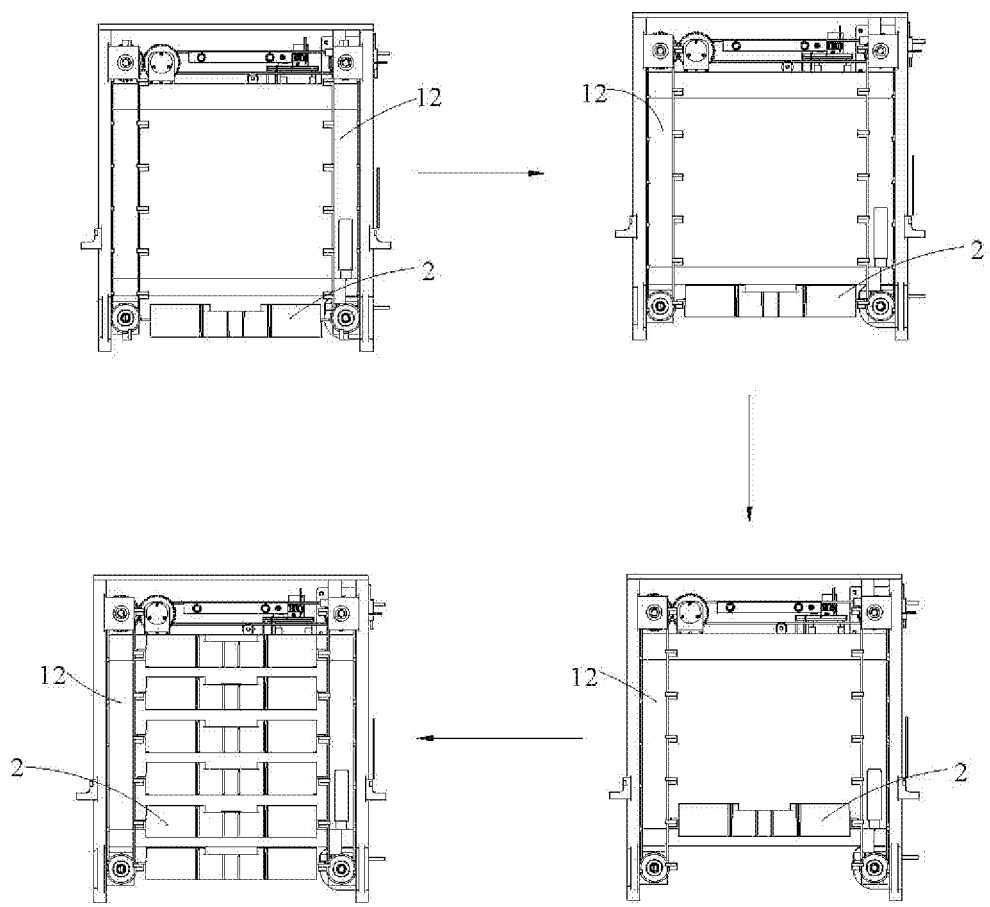
FIG. 10 is a structural schematic diagram that a consumable box is received and is lifted in a consumable box lifting mechanism.

Optionally, as shown in FIG. 7, the lifting frame structure 122 includes a lifting border component 1221; the lifting drive structure 123 is mounted on the lifting border component 1221; the lifting transmission structure 121 is mounted in the lifting border component 1221. The lifting border component 1221 can play a supporting role to support various parts in the consumable box lifting mechanism 12. Optionally, the lifting border component 1221 is a cubic border surrounded by multiple columns; the lifting drive structure 123 is fixed on the columns; the lifting transmission structure 121 is movably provided on the columns. Optionally, the lifting frame structure 122 includes multiple lifting surrounding plates 1222; the multiple lifting surrounding plates 1222 are oppositely arranged at two sides of the lifting border component 1221. Specifically, the lifting surrounding plates 1222 are provided on the columns of the lifting border component 1221, provided that the lifting surrounding plates 1222 are and the lifting transmission structure 121 do not interfere when moving. Meanwhile, the lifting surrounding plates 1222 also have a protective effect, preventing the consumables in the consumable boxes 2 in the lifting frame structure 122 from being contaminated, and guaranteeing accurate detection results of the chemiluminescence detector. Preferably, the number of the lifting surrounding plates 1222 is two; the two lifting surrounding plates 1222 are oppositely arranged at the outer side of a rotating component 1211. Optionally, the lifting frame structure 122 further includes multiple lifting side plates 1223; the multiple lifting side plates 1223 are oppositely arranged at the other two sides of the lifting border component 1211. That is to say, the lifting side plates 1223 and the lifting surrounding plates 1222 are arranged at different sides. The lifting side plates 1223 can prevent the consumable boxes 2 from shaking and deflecting, and accordingly limit the position of the consumable boxes 2 in the lifting frame structure 122, thereby guaranteeing reliability of the lifting transmission structure 121 for lifting the consumable boxes 2. Preferably, the number of the lifting side plates 1223 is two; the two lifting side plates 1223 are oppositely arranged, and located at the other two sides of the lifting frame structure 122, adjacent to the lifting surrounding plates 1222. Further, the width of the lifting side plates 1223 is less than the width of the lifting surrounding plates 1222. The lifting surrounding plates 1222 and the lifting side plates 1223 surround at the periphery of the lifting border component 1221, and the lifting frame structure 122 is a half-surrounded structure. In this way, the operator can conveniently observe the situation in the lifting frame structure 122 through a space between the lifting side plates 1223 and the lifting surrounding plates 1222, so as to ensure that the consumable box lifting mechanism 12 operates stably. As shown in FIG. 8, in another embodiment of the present disclosure, the lifting frame structure 122 can merely include the lifting border component; that is to say, the consumable boxes 2 can be lifted and transmitted without the lifting surrounding plates 1222 and the lifting side plates 1223 in the above embodiment. The lifting drive structure 123 is mounted on the lifting border component; the lifting transmission structure 121 is mounted in the lifting border component. The lifting border component can play the supporting role to support various parts in the consumable box lifting mechanism 12.

Further, the lifting drive structure 123 includes a lifting drive motor 1231 and a lifting transmission component 1232; the lifting drive motor 1231 is fixed on the lifting frame structure 122; the lifting transmission component 1232 is transmissibly provided on the lifting frame structure 122; the lifting transmission component 1232 is mounted at the output end of the lifting drive motor 1231; the lifting transmission component 1232 is in transmission connection with the lifting transmission structure 121, so as to transmit the power of the lifting drive motor 1231 to the lifting transmission structure 121.

The lifting transmission structure 121 includes two rotating components 1211 and multiple rotating support portions 1212; the two rotating components 1211 are symmetrically arranged in the lifting frame structure 122; the multiple rotating support portions 1212 are respectively provided on the two rotating components 1211, and the multiple rotating support portions 1212 on each rotating component 121 are arranged intervals along the rise-fall direction. The two rotating components 1211 are respectively arranged at two opposite sides of the lifting frame structure 122; the two opposite rotating support portions 1212 on the two rotating components 1211 can support two ends of the consumable boxes 2; the lifting drive structure 123 drives the rotating components 1211, and the multiple rotating support portions 1212 are driven to move synchronously, and each of the rotating support portions 1212 respectively drive corresponding consumable boxes 2 which are supported by corresponding each of the rotating support portions 1212 to rise or fall. The rotating support portions 1212 at corresponding positions on the two rotating components 1211 are arranged in a coplanar manner; the rotating support portions 1212 at corresponding positions on the two rotating components 1211 jointly support the consumable boxes 2. As the rotating support portions 1212 are arranged on the rotating components 1211, a certain distance exists between adjacent consumable boxes 2 supported by the rotating support portions 1212; thus, the consumable boxes 2 can be continuously loaded under the rotating components 1211.

It may be understood that, the rotating components 1211 is able to drive the rotating support portions 1212 to rotate through a rotary motion. The two rotating components 1211 is able to drive the rotating support portions 1212 thereon to move; to facilitate description of movement of the rotating support portions 1212, the opposite sides of the two rotating components 1211 serve as rotating inner sides, while the non-opposite sides of the two rotating components 1211 serve as rotating outer sides. When some rotating support portions 1212 do rising movement at the rotating inner side of the rotating components 1211, others rotating support portions 1212 do falling movement at the rotating outer side; thus, the rotating support portions 1212 rotate around the rotating components 1211. Specifically, when the consumable box automatic transmission device 1 needs to convey a consumable box 2 to the preset position, the rotating components 1211 drive the rotating support portions 1212 to lift the consumable box 2 from the lesser top layer of the lifting border component 1221 to the top layer; when needing to convey a consumable box 2 to the preset position again, the rotating components 1211 drive the rotating support portions

1212 to rise at the rotating inner side, and lift the consumable box 2 at the lesser top layer of the lifting frame structure 122 to the top layer of the lifting frame structure 122; meanwhile, the rotating components 1211 drive the rotating support portions 1212 that support to convey the consumable box 2 to move from the rotating inner side to the rotating outer side and locate at the top layer of the lifting frame structure 122; when the consumable boxes 2 on the lifting transmission structure 121 are repetitively conveyed and lifted, the rotating support portions 1212 continuously fall at the rotating outer side, and gradually move to the bottom of the lifting frame structure 122. When the consumable box lifting mechanism 12 needs to load a consumable box 2, the rotating support portions 1212 at the rotating outer side rotate around the rotating components 1211; thus, the rotating support portions 1212 gradually return to the rotating inner side from the bottom of the rotating components 1211; the rotating support portions 1212 receive the consumable box 2 conveyed by the storage rise-fall component 1111 when gradually returning to the rotating inner side from the bottom of the rotating components 1211, thereby implementing continuous loading of the consumable boxes 2. Besides, the rotating support portions 1212 of the two rotating components 1211 at the rotating inner side synchronously rise or fall to ensure that the consumable box 2 stably rises or falls in the lifting frame structure 122.

The lifting transmission component 1232 is in transmission connection with the output shaft of the lifting drive motor 1231 and the two rotating components 1211; the lifting drive motor 1231 drives the lifting transmission component 1232 to move; the lifting transmission component 1232 drives the rotating components 1211 to move; thus, the rotating components 1211 drive the rotating support portions 1212 thereon to rise or fall, and the consumable boxes 2 rise and fall through the rotating support portions 1212. When the consumable boxes 2 are lifted, the lifting drive motor 1231 drives the lifting transmission component 1232 to move; the lifting transmission component 1232 drives the rotating components 1211 and the rotating support portions 1212 on the rotating components 1211 to move; thus, the rotating support portions 1212 drive the consumable boxes 2 to move; when one of the consumable boxes 2 at the top layer of the rotating components 1211 is conveyed, the rotating components 1211 is able to lift a consumable box 2 at the lesser top layer to the top layer; in addition, when the consumable boxes 2 on the rotating support portions 1212 of the rotating components 1211 are used up or have a small amount, the rotating components 1211 receive new consumable boxes 2 conveyed by the storage rise-fall component 1111 at the transmission position through the rotating support portions 1212; thus, the consumable boxes 2 are conveyed to the consumable box lifting mechanism 12 from the consumable box storage mechanism 11.

Besides, the lifting transmission component 1232 is a lifting synchronous belt component, a chain wheel transmission, a gear transmission component, a multi-stage gear transmission component, a two-sided gear synchronous belt, a synchronous pulley structure or any other structure that can implement transmission of movement. Preferably, the lifting transmission component 1232 includes two lifting synchronous pulleys 12322, a lifting synchronous belt 12321 and two lifting transmission gears 12323. One lifting synchronous pulley 12322 is in transmission connection with a rotating component 1211, and is mounted at an output end of the lifting drive motor 1231; the other lifting synchronous pulley 12322 is rotatably provided on the gear shaft of a lifting transmission gear 12323, which is rotatably mounted on the lifting frame structure 122; the other lifting transmission gear 12323 is in transmission connection with the other rotating component 1211; the two lifting transmission gears 12323 are engaged. The lifting synchronous belt 12321 is provided on the two lifting synchronous pulleys 12322 in a sleeping manner. The lifting drive motor 1231 drives one lifting synchronous pulley 12322 to move; the lifting synchronous pulley 12322 drives the lifting synchronous belt 12321 and the other lifting synchronous pulley 12322 to move synchronously; meanwhile, the lifting synchronous pulley 12322 drives the lifting transmission gear 12323 connected with the lifting synchronous pulley 12322 to move synchronously; thus, the lifting transmission gear 12323 drives the other lifting transmission gear 12323 engaged to move. In this way, the two lifting synchronous pulleys 12322 and the two lifting transmission gears 12323 cooperate to drive the rotating components 1211 to rotate concurrently; accordingly, the rotating support portions 1212 rotate around the rotating components 1211; besides, the rotating support portions 1212 on the two rotating components 1211 synchronously rise or fall at the rotating inner side, thereby implementing the reception, lifting and conveyance of the consumable boxes 2. Optionally, the consumable box lifting mechanism 12 further includes a tension structure; the tension structure is provided on the lifting frame structure 122; the tension structure is configured to tense the lifting synchronous belt 12321, so as to ensure the transmission reliability of the lifting transmission component 1232.

Specifically, the rotating component 1211 includes a rotating belt 12111, two rotating pulleys and two rotating shafts 12112; the two rotating pulleys are respectively provided on the two rotating shafts 12112 in a sleeving manner; the two rotating shafts 12112 are rotatably provided on the lifting frame structure 122; one end of a rotating shaft 12112 stretches out of the lifting frame structure 122 and is in transmission connection with the lifting drive structure 123; the lifting drive structure 123 drives the rotating shaft 12112, thereby driving the rotating belt 12111 to rotate. The two ends of the rotating shafts 12112 are mounted on the lifting frame structure 122 through a rolling bearing; one rotating shaft 12112 is arranged at the top layer of the lifting frame structure 122, while the other rotating shaft 12112 is arranged at a bottom of the lifting frame structure 122; the rotating belt 12111 is provided on the two rotating pulleys in a sleeving manner; thus, when rotating, the two rotating shafts 12112 is able to drive the rotating pulleys thereon to rotate; accordingly, the rotating pulleys drive the rotating belt 12111 to rotate, and the rotating support portions 1212 on the rotating belt 12111 rise and fall. One end of a rotating shaft 12112 stretches to connect a lifting synchronous pulley 12322; then, when the lifting drive motor 1231 drives the lifting synchronous pulley 12322 to rotate, the lifting synchronous pulley 12322 drives the other lifting synchronous pulley 12322 to synchronously move through the lifting synchronous belt 12321 when driving the rotating shaft 12112 of a rotating component 1211; the other lifting synchronous pulley 12322 is able to drive the two transmission gears 12323 to transmit in an engaged manner and drive the rotating shaft 12112 of the other rotating component 1211 to move; accordingly, the two rotating belts 12111 can synchronously rise or fall and drive the rotating support portions 1212 thereon to synchronously rise or fall at the rotating inner side. Optionally, the rotating pulleys and the rotating shafts 12112 can be integrated or separated; when they are separated, the rotating pulleys are fixed on the rotating shafts 12112 through key connection or pin connection. Of course, in other embodiments of the present disclosure, either rotating component 1211 can correspond to a lifting drive motor 1231, provided that the two rotating components 1211 synchronously rise or fall at the rotating inner side. Further, the rotating shafts 12112 are provided with a limiting barrier 121121 at both sides of the rotating belt 12111; the limiting barrier 121121 limits movement of the rotating shafts 12112 along the axial direction, thereby preventing the rotating belt 12111 from being displaced, and guaranteeing reliable transmission of the consumable boxes 2.

In an embodiment of the present disclosure, the rotating belt 12111 is a synchronous belt, the rotating shafts 12112 are rotating shafts, and the rotating shafts 12112 are matched with the rotating belt 12111 to implement a rotary motion; preferably, the rotating belt 12111 is a synchronous belt with tooth portions, the rotating shafts 12112 are rotating shafts with a rotating gear, and the rotating gear is engaged with the synchronous belt with tooth portions to implement a rotary motion. In another embodiment of the present disclosure, the rotating belt 12111 is a synchronous chain, and the rotating shafts 12112 are rotating shafts with a chain wheel. Of course, in other embodiments of the present disclosure, the rotating belt 12111 can also be any other structure that can implement a rotary motion. The rotating support portions 1212 are support plates, and can also be any other structures that can support the consumable boxes 2, such as lug bosses, clamping jaws or suspension plates.

It may be understood that, a consumable box 2 is provided with ear-like portions at two sides; after the consumable box lifting mechanism 12 receives the consumable box 2, the two rotating support portions 1212 concurrently contact with the lugs at the two sides of the consumable box 2, thereby guaranteeing that the consumable box 2 is supported reliably, and preventing dropping. Additionally, when the lifting transmission structure 121 lifts the consumable box upward, the rotating components 1211 drive the rotating support portions 1212 at the rotating inner side to rise, so that the consumable box 2 is lifted; in this way, the consumable boxes 2 are continuously conveyed to the top layer of the consumable box lifting mechanism 12.

In this embodiment, when the consumable box automatic transmission device 1 transmits the consumable boxes 2, if no consumable box 2 is in the consumable box lifting mechanism 12, the rotating components 1211 drive the rotating support portions 1212 at the rotating outer side to move to the bottom of the rotating components 1211, and the rotating support portions 1212 are in a vertical status; then, the storage drive motor drives the storage rise-fall component 1111, thereby driving the storage support portion 1112 and multiple consumable boxes 2 laminated thereon to rise, so that the highest one of the consumable boxes 2 on the storage support portion 1112 is moved to the transmission position; then, the rotating components 1211 move upward and drive the rotating support portions 1212 to move towards the rotating inner side and reach the transmission position; thus, the rotating support portions 1212 gradually become horizontal and locate under the ear-like portions of the consumable boxes 2, thereby implementing reception of the consumable boxes 2. To receive the consumable boxes 2 again, the rotating components 1211 drive the rotating support portions 1212 to repetitively execute the above operation; the consumable box lifting mechanism 12 stops receiving the consumable boxes 2 when the highest one of the consumable boxes 2 on the lifting transmission structure 121 moves to the lesser top layer of the lifting frame structure 122.

When one or a few consumable boxes 2 are left on the lifting transmission structure 121, the rotating components 1211 drive the rotating support portions 1212 at the rotating inner side to fall, and drive the consumable boxes 2 at the rotating inner side to fall; when the lowest one of the consumable boxes 2 on the rotating components 1211 moves to the transmission position, the rotating components 1211 move upward for a half layer, so that the rotating support portions 1212 at a bottom of the rotating components 1211 switch to a vertical status from the horizontal status; then, the storage drive motor drives the storage rise-fall component 1111, thereby driving the storage support portion 1112 and multiple consumable boxes 2 thereon to rise, so that the highest one of the consumable boxes 2 on the storage support portion 1112 moves to the transmission position; then the rotating components 1211 rise, and the rotating support portions 1212 gradually enter a horizontal status at the rotating inner side and locate under the ear-like portions of the consumable boxes 2, thereby implementing the reception of the consumable boxes 2; then, the rotating components 1211 again move upward for a half layer and repeat the operation of receiving the consumable boxes 2; through such repetition, the consumable box lifting mechanism 12 stops receiving the consumable boxes 2 when the highest one of the consumable boxes 2 on the lifting transmission structure 121 moves to the lesser top layer of the lifting frame structure 122. It may be understood that, the rotating components 1211 move upward for a half layer when receiving the consumable boxes 2.

Specifically, the lifting drive motor 1231 moves and drives the rotating shafts 12112 of the rotating components 1211 through the lifting transmission component 1232 to rotate; accordingly, the rotating shafts 12112 drive the rotating belt 12111 to rotate, and the rotating support portions 1212 on the rotating belt 12111 rise and fall; the rotating support portions 1212 can gradually move from the bottom of the consumable box lifting mechanism 12 to the top layer of the consumable box lifting mechanism 12, and gradually returns to the bottom of the consumable box lifting mechanism 12; the rotating support portions 1212 can implement reception and lifting of the consumable boxes 2 during the process of a rotary motion. The rotating support portions 1212 can implement lifting of the consumable boxes 2 when moving from the bottom of the consumable box lifting mechanism 12 to the lesser top layer of the consumable box lifting mechanism 12; when the consumable box automatic transmission device 1 needs to convey the consumable boxes 2 to the preset position, the rotating support portions 1212 lift the consumable boxes 2 from the lesser top layer to the top layer; when the consumable boxes 2 need to be conveyed to the preset position again, the lifting drive motor 1231 drives the rotating components 1211, thereby driving the rotating support portions 1212 to move upward for one layer; thus, the consumable boxes 2 at the lesser top layer of the consumable box lifting mechanism 12 move to the top layer, and the consumable boxes are conveyed continuously; when the consumable box lifting mechanism 12 needs to supplement the consumable boxes 2, the rotating components 1211 drive the rotating support portions 1212 to move from both sides to the centre at a bottom of the consumable box lifting mechanism 12 and support the highest one of the consumable boxes 2 of the storage rise-fall component 1111 at the transmission position, thereby finishing the reception.

Further, the multiple rotating support portions 1212 are uniformly arranged at the periphery of the two rotating belts 12111. Thus, the distance between two adjacent rotating support portions 1212 is constant, and the distance that the rotating belts 12111 rise every time is constant, thereby guaranteeing reliable reception and lifting of the consumable boxes 2. Besides, the rotating support portions 1212 at corresponding positions on the two rotating belts 12111 are arranged in a coplanar manner. Thus, the consumable boxes 2 are balanced, thereby preventing the consumable boxes 2 from being inclined, and guaranteeing reliable transmission.

Optionally, the lifting drive structure 123 further includes a braking unit 1233; the braking unit 1233 is configured to brake the rotating shafts 12112 of the rotating components 1211. It may be understood that, the braking unit 1233 can brake any one of the four rotating shafts 12112 of the two rotating components 1211. When the lifting drive motor 1231 runs properly, the braking unit 1233 does not work, but the rotating shafts 12112 can rotate properly; when the lifting drive motor 1231 is powered off, the braking unit 1233 can clasp any one of the rotating shafts 12112, so that the lifting transmission structure 121 stops moving, thereby guaranteeing reliable operation of the consumable box lifting mechanism 12, and guaranteeing reliable movement of the lifting transmission structure 121. Preferably, the braking unit 1233 is a non-excitation brake; of course, the braking unit 1233 can also be any other structure that can implement output end brake of the lifting drive motor 1231.

As an implementable embodiment, the consumable box lifting mechanism 12 further includes a lifting detection structure 124; the lifting detection structure is provided on the lifting frame structure 122. The lifting detection structure 124 is configured to ensure the initial status of the rotating support portions 1212 and ensure whether a consumable box 2 exists in the detection area. Further, the lifting detection structure 124 includes a lifting locating unit 1241; the lifting locating unit 1241 is matched with the rotating support portions 1212, locates the rotating support portions 1212, and carries out initial detection of the rotating support portions 1212. The lifting locating unit 1241 is configured to detect the status of the rotating support portions 1212. When the rotating support portions 1212 is matched with the lifting locating unit 1241, the rotating support portions 1212 are under a horizontal status, and the rotating support portions 1212 at the rotating inner side and the rotating outer side all are under a horizontal status, thereby guaranteeing that the rotating support portions 1212 are under a horizontal status when the system is initialized, and guaranteeing that the rotating support portions 1212 reliably support the consumable boxes. If the lifting locating unit 1241 is separated from the rotating support portions 1212 when the system is initialized, some rotating support portions 1212 are inclined; the lifting drive motor 1231 drives the lifting transmission component 1232, thereby driving the rotating components 1211 to move; thus, the rotating components 1211 drive the rotating support portions 1212 to rise or fall so as to match with the lifting locating unit 1241, and ensure accurate position of the rotating support portions 1212. Besides, the transmission position where the consumable box lifting mechanism 12 receives the consumable boxes 2 is lower than a position where the rotating support portions 1212 at a bottom of the consumable box lifting mechanism 12 are under a horizontal status.

As the rotating support portions 1212 are uniformly distributed on the rotating components 1211, and the distance between two adjacent rotating support portions 1212 is greater than the height of one consumable box 2, a rotating support portion 1212 is under a horizontal status after cooperating with the lifting locating unit 1241, and the rest rotating support portions 1212 all are under a horizontal status. When the rotating belts 12111 drive the rotating support portions 1212 to move to a location area of the lifting locating unit 1241, the rotating support portions 1212 are under a horizontal status; then a subsequent operation can be carried out, for example, to detect whether a consumable box 2 is on the rotating support portions 1212. Preferably, the lifting locating unit 1241 is a locating optical coupler; the rotating support portions 1212 are provided with locating lug bosses; when the rotating support portions 1212 move to the location area of the locating optical coupler, the locating lug bosses are located in the locating optical coupler, and prevent signals of the locating optical coupler, indicating that the rotating support portions 1212 move in place; then, the rotating support portions 1212 are under a horizontal status. Of course, in other embodiments of the present disclosure, the lifting locating unit 1241 can be a locating lug boss or any other structure that can implement location of the rotating support portions 1212; the rotating support portions 1212 are provided with a structure cooperating with the lifting locating unit 1241. In this embodiment, the lifting locating unit 1241 is located at the top layer of the lifting frame structure 122; of course, in other embodiments of the present disclosure, the lifting locating unit 1241 can also be located in the central area or any other position of the lifting frame structure 122.

Further, the lifting detection structure 124 further includes a first lifting detection unit 1242; a detection area of the first lifting detection unit 1242 is located at the top layer of the lifting frame structure 122. The rotating components 1211 drives the rotating support portions to move to the detection area of the first lifting detection unit 1242; the first lifting detection unit 1242 can detect whether a consumable box 2 exists on the rotating support portions in the detection area. The first lifting detection unit 1242 is configured to detect whether a consumable box 2 is at the top layer of the lifting frame structure 122. Preferably, the first lifting detection unit 1242 is a first lifting sensor; the first lifting sensor is arranged at the top layer of the lifting frame structure 122; the detection area of the first lifting sensor is correspondingly located at the top layer of the lifting frame structure 122, so as to detect whether a consumable box 2 exists. Of course, in other embodiments of the present disclosure, the first lifting detection unit 1242 can also be any other structure that can detect whether a consumable box 2 exists.

In this embodiment, the detection area of the first lifting detection unit 1242 is adjacent to the location area of the lifting locating unit 1241. When the lifting locating unit 1241 is matched with the rotating support portions 1212, the space between the rotating support portions 1212 at corresponding positions on the two rotating components 1211 is in the detection area of the first lifting detection unit 1242; then, the first lifting detection unit 1242 can detect whether a consumable box 2 exists between the rotating support portions 1212; if the first lifting detection unit 1242 detects a consumable box 2, the rotating components 1211 stops moving.

Further, the lifting detection structure 124 further includes a second lifting detection unit 1243; a detection area of the second lifting detection unit 1243 is located at a bottom of the lifting frame structure 122; the rotating components 1211 drive the rotating support portions to move to the detection area of the second lifting detection unit 1243; the second lifting detection unit 1243 can detect whether a consumable box 2 exists on the rotating support portions in the detection area. The second lifting detection unit 1243 is configured to detect whether a consumable box 2 is at a bottom of the lifting frame structure 122. The rotating components 1211 drive a consumable box 2 to move to the bottom of the lifting frame structure 122; the second lifting detection unit 1243 can detect whether the consumable box 2 exists at a bottom.

The lifting locating unit 1241, the first lifting detection unit 1242 and the second lifting detection unit 1243 are configured to count the number of consumable boxes 2 in the consumable box lifting mechanism 12. Before every count, a control device of the chemiluminescence detector can control the lifting drive motor 1231 to drive the rotating support portions 1212 of the rotating components 1211 to move to the lifting locating unit 1241; then the rotating components 1211 are wholly driven to move upward layer by layer; when the first lifting detection unit 1242 detects a consumable box 2, the rotating components 1211 are wholly driven to move downward layer by layer till the second lifting detection unit 1243 detects a consumable box 2; according to the number of downward movement layers and the number of consumable boxes stored in the consumable box lifting mechanism 12, the number of consumable boxes 2 in the consumable box lifting mechanism 12 is calculated. Besides, if the first lifting detection unit 1242 does not detect any consumable box 2 all the time when the lifting transmission structure 121 moves from the bottom of the lifting frame structure 122 to the top layer of the lifting frame structure 122, no consumable box 2 exists in the consumable box lifting mechanism 12; or, if the second lifting detection unit 1243 does not detect any consumable box 2 when the lifting transmission structure 121 moves from the top layer of the lifting frame structure 122 to the bottom of the lifting frame structure 122, no consumable box 2 exists in the consumable box lifting mechanism 12; that is to say, the number of consumable boxes 2 in the consumable box lifting mechanism 12 is zero, thereby preventing the lifting transmission structure 121 from idling, and guaranteeing operational performance. Optionally, the number of the layers that the lifting transmission structure 121 moves or the step number that the lifting drive motor 1231 moves can be calculated through a counter or a counting module, and the like, thereby counting the number of the consumable boxes 2 in the consumable box lifting mechanism 12.

It is to be noted that, the consumable box storage mechanism 11 transmits consumable boxes 2 to the consumable box lifting mechanism 12, and when being full, the consumable box lifting mechanism 12 stops receiving the consumable boxes 2; when the consumable boxes 2 in the consumable box lifting mechanism 12 are used up, the consumable box storage mechanism 11 continues to transmit consumable boxes 2 to the consumable box lifting mechanism 12; or, when at least one consumable box 2 is left in the consumable box lifting mechanism 12, the consumable box lifting mechanism 12 drives the lifting transmission structure 121 to make the at least one consumable box 2 fall above the transmission position; then, the lifting transmission structure 121 receives consumable boxes 2; thus, no vacancy exists between two adjacent consumable boxes 2, thereby implementing continuous conveyance of the consumable boxes 2, and providing convenience for counting the number of the consumable boxes 2. In addition, the lifting drive motor 1231 is a stepping motor; when a consumable box 2 is loaded into the lifting transmission structure 121, the number of the consumable boxes 2 left in the lifting transmission structure 121 is counted through the step number of the lifting drive motor 1231, thereby providing convenience for counting the number of the consumable boxes 2. When the chemiluminescence detector is started, the actual number of unused consumable boxes 2 in the consumable box automatic transmission device 1 needs to be counted; the consumable box storage mechanism 11 and the consumable box lifting mechanism 12 are counted respectively; then sum of the number of consumable boxes 2 in the consumable box storage mechanism 11 and the number of consumable boxes 2 in the consumable box lifting mechanism 12 is the actual number of the unused consumable boxes 2 in the consumable box automatic transmission device 1.

Referring to FIG. 1 to FIG. 3, as an implementable embodiment, the consumable box automatic transmission device 1 further includes a consumable box recycling mechanism 13. The consumable box recycling mechanism 13 is located under the preset position; the consumable box recycling mechanism 13 is able to recycle consumable boxes 2 at the preset position. The consumable box recycling mechanism 13 is configured to recycle and store the consumable boxes 2; the consumable boxes 2 can be conveyed to the consumable box recycling mechanism 13, and the consumable box recycling mechanism 13 implements recycling and storage of the consumable boxes 2. Used consumable boxes 2 can be stored in the consumable box recycling mechanism 13; when the consumable box recycling mechanism 13 is fully or partially filled with the consumable boxes 2, the consumable boxes 2 can be taken out from the lower part of the consumable box recycling mechanism 13, thereby implementing continuous recycling of the consumable boxes 2 and facilitating use. Preferably, the consumable box recycling mechanism 13 is adjacent to the consumable box storage mechanism 11 and the consumable box lifting mechanism 12 that are arranged from top to bottom, thereby facilitating conveyance of the consumable boxes 2, and reducing occupation space.

Preferably, the consumable box recycling mechanism 13 includes a recycling storage structure and a recycling transmission structure 133; the recycling transmission structure 133 is movably provided in the recycling storage structure. The recycling storage structure is a main part configured to recycle and store the consumable boxes 2; the recycled consumable boxes 2 are stored in the recycling storage structure; the recycling storage structure is provided with a recycling channel; the consumable boxes 2 are recycled and stored in the recycling channel. The recycling transmission structure 133 is configured to receive and transmit the consumable boxes 2; the recycling transmission structure 133 moves in the recycling channel of the recycling storage structure in a rise-fall manner; specifically, the recycling transmission structure 133 receives the consumable boxes 2 at the top layer of the recycling storage structure, and transfers the consumable boxes 2 from the top layer of the recycling storage structure to the bottom. Besides, when the recycling transmission structure 133 receives one consumable box 2 at the top layer of the recycling storage structure, the recycling transmission structure 133 returns to the bottom of the recycling storage structure; when another consumable box 2 is recycled, the recycling transmission structure 133 moves upward to the top layer of the recycling storage structure; the recycling transmission structure 133 receives the consumable box 2; the consumable box 2 falls on the highest consumable box 2 of the recycling transmission structure 133; then the recycling transmission structure 133 again returns to the bottom of the recycling storage structure. It may be understood that, when the recycling transmission structure 133 receives a used consumable box 2, the recycling transmission structure 133 moves to the top layer of the recycling storage structure; the recycling transmission structure 133 again returns to the bottom of the recycling storage structure after receiving the consumable box 2. In this way, a problem can be prevented that the consumable box 2 drops when the recycling transmission structure 133 is in a central position due to equipment power failure. As the used consumable boxes 2 are arranged and stored in a laminated manner in the recycling storage structure, large capacity storage of the consumable boxes 2 is implemented, and occupancy in the layout position of the instrument is minimized; therefore, the structure of the consumable box automatic transmission device 1 is compact, and the overall size of the chemiluminescence detector is reduced.

In addition, the consumable box automatic transmission device 1 further includes a consumable box positioning and dropping mechanism 14; the consumable box positioning and dropping mechanism 14 is arranged above the consumable box recycling mechanism 13. The consumable boxes 2 on the consumable box lifting mechanism 12 can be transmitted to the consumable box positioning and dropping mechanism 14, and drop into the consumable box recycling mechanism 13 through the consumable box positioning and dropping mechanism 14. The consumable box positioning and dropping mechanism 14 can also facilitate location of the consumable boxes 2, so that the position of the consumable boxes 2 is always fixed, thereby providing convenience for the chemiluminescence detector to take the consumables out of the consumable boxes 2 at the consumable box 2 drop mechanism 14. When the consumables in the consumable boxes 2 are taken out, the consumable boxes 2 are recycled; the consumable boxes 2 can drop through the consumable box positioning and dropping mechanism 14 and be stored in the consumable box recycling mechanism 13, thereby facilitating recycling of the consumable boxes 2.

It is to be noted that, the preset position is a position on the consumable box positioning and dropping mechanism 14. The consumable boxes 2 on the consumable box lifting mechanism 12 are conveyed to the consumable box positioning and dropping mechanism 14; the chemiluminescence detector grabs the consumables in the consumable boxes 2 on the consumable box positioning and dropping mechanism 14; when the consumables in the consumable boxes 2 are removed, the consumable box positioning and dropping mechanism 14 drops the consumable boxes 2 into the consumable box recycling mechanism 13 for storage. Of course, in other embodiments of the present disclosure, the preset position can also be a position at the top layer of the consumable box lifting mechanism 12. The chemiluminescence detector grabs the consumables in the consumable boxes 2 at the top layer of the consumable box lifting mechanism 12; when the consumables in the consumable boxes 2 are removed, the used consumable boxes 2 at the top layer of the consumable box lifting mechanism 12 are conveyed to the consumable box positioning and dropping mechanism 14; the consumable box positioning and dropping mechanism 14 drops the consumable boxes 2 into the consumable box recycling mechanism 13 for storage. Of course, the preset position can also be a position on the other parts of the chemiluminescence detector.

Referring to FIG. 1 to FIG. 3, further, the consumable box automatic transmission device 1 further includes a push mechanism 15. The push mechanism 15 is provided on the consumable box lifting mechanism 12; the push mechanism 15 is able to push a consumable box 2 at the top layer of the consumable box lifting mechanism 12 to the preset position. In an embodiment of the present disclosure, the push mechanism 15 is able to push the consumable boxes 2 on the consumable box lifting mechanism to the consumable box positioning and dropping mechanism 14. Besides, when the push mechanism 15 pushes the consumable boxes 2 to the consumable box positioning and dropping mechanism 14, the push mechanism 15 stops moving; the push mechanism 15 and the consumable box positioning and dropping mechanism 14 locate the consumable boxes 2, thereby guaranteeing accurate position of the consumables to be grabbed by the chemiluminescence detector in the consumable boxes 2; when the consumables in the consumable boxes 2 are completely grabbed, the push mechanism 15 is reset; the consumable box positioning and dropping mechanism 14 drops the used consumable boxes 2 into the consumable box recycling mechanism 13 for storage; then, the push mechanism 15 again pushes another consumable box 2 at the top layer of the consumable box lifting mechanism 12 to the consumable box positioning and dropping mechanism 14.

Figure 11:
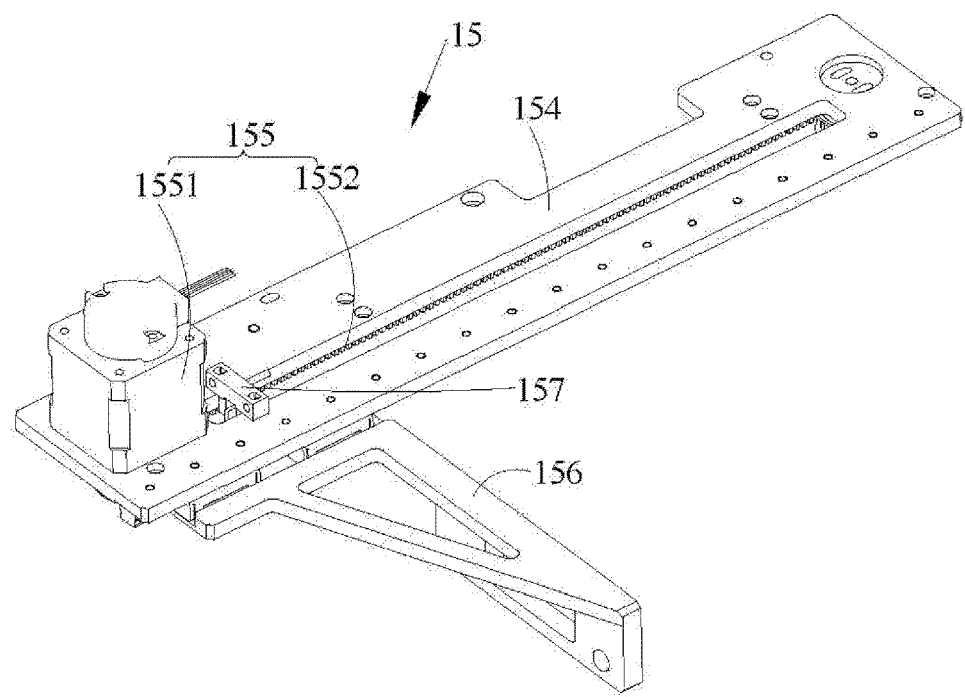
FIG. 11 is a stereogram of a push mechanism In an embodiment of the consumable box automatic transmission device as shown in FIG. 1.

Referring to FIG. 1 and FIG. 11, in an embodiment of the present disclosure, the push mechanism 15 includes a push bottom plate 154, a push transmission structure 155 provided on the push bottom plate and a push plate 156 in transmission connection with the push transmission structure 155. The push bottom plate 154 is mounted on the lifting surrounding plate 1222 of the lifting frame structure 112; the push bottom plate 154 can also support the push transmission structure 155. The push transmission structure includes a push transmission motor 1551 and a push drive component 1552; the push transmission motor 1551 is provided on the push bottom plate 154; the push drive component 1552 is in transmission connection with the output shaft of the push transmission motor 1551 and the push plate 156. The push transmission motor 1551 is able to drive the push drive component 1552, thereby driving the push plate 156 to move; thus, the push plate 156 pushes a consumable box 2 at the top layer of the consumable box lifting mechanism 12 to a preset position, namely the consumable box positioning and dropping mechanism 14. Preferably, the push drive component 1552 can be a structure of cooperative synchronous transmission belt and synchronous transmission pulley; of course, the push drive component 1552 can also be a structure that can output linear movement, such as a gear and rack structure, a connecting rod structure, a screw rod structure, a stroke multiplying structure and a double platform output structure.

Further, the push bottom plate is provided with a push guide groove; the push mechanism further includes a push guide block; the push guide block can move along the push guide groove; the push guide groove is mounted on the push drive component 1552; when the push drive component 1552 drives the push guide block to move along the push guide groove, the movement of the push drive component 1552 is guided, thereby preventing the position of the push plate 156 from being displaced, and guaranteeing that the push plate 156 pushes the consumable boxes 2 stably and reliably. Further, the push mechanism 15 further includes a push initialization detection element 157; the push initialization detection element 157 is provided on the push bottom plate 154, and is close to the push transmission motor 1551; the push initialization detection element 157 is configured to initialize the push transmission motor 1551, so that the push plate 156 is at an initial position. Preferably, the push initialization detection element 157 can be a push optical coupler, and of course, can be any other structure that can implement initialization detection of the push transmission motor 1551.

Figure 12:
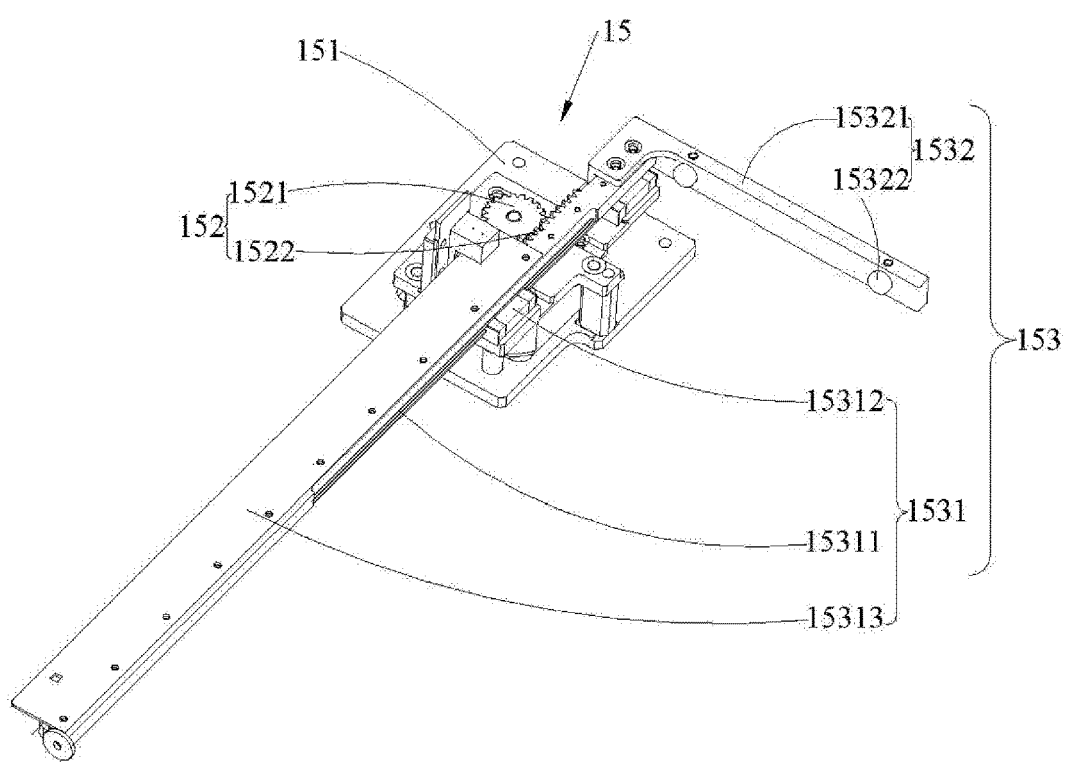
FIG. 12 is a stereogram of a push mechanism in another embodiment of the consumable box automatic transmission device as shown in FIG. 1.

Referring to FIG. 12, in another embodiment of the present disclosure, the push mechanism 15 includes a push mounting plate 151, a push drive structure 152 and a push sliding structure 153; the push mounting plate 151 is located on the lifting frame structure 122. The push drive structure 152 and the push sliding structure 153 are provided on the push mounting plate 151; the push drive structure 152 is in transmission connection with the push sliding structure 153. The push drive structure 152 is able to drive the push sliding structure 153 to move, so as to push a consumable box 2 at the top layer of the consumable box lifting mechanism 12 to a preset position, namely the consumable box positioning and dropping mechanism 14. The push mechanism 15 in this embodiment is mounted on the consumable box lifting mechanism 12 as shown in FIG. 8, and is configured to push the consumable boxes 2.

Specifically, the push drive structure 152 includes a push drive motor and a push transmission component; the push drive motor is provided on the push mounting plate 151; the push transmission component is movably provided on the push mounting plate 151; the push transmission component is mounted on the output end of the push drive motor; the push transmission component is in transmission connection with the push sliding structure 153. The push transmission motor drives the push drive component, thereby driving the push sliding structure 153 to move; thus, the push sliding structure 153 pushes a consumable box 2 at the top layer of the consumable box lifting mechanism 12 to the consumable box positioning and dropping mechanism 14.

The push sliding structure 153 includes a push sliding component 1531 and a push component 1532; the push sliding component 1531 is fixedly provided on the push mounting plate 151, and is in transmission connection with the push transmission component; the push component 1532 is mounted on the push sliding component 1531. The push drive motor drives the push transmission component, thereby driving the push sliding component 1531 to move; thus, the push sliding component 1531 drives the push component 1532 thereon to push the consumable boxes 2.

Preferably, the push transmission component is a gear transmission component, including a push gear 1521 and a push rack 1522; the push sliding component 1531 includes a push slide rail 15311 and a push slide block 15312. The push slide block 15312 is fixed on the push mounting plate 151; the push slide rail 15311 slidably is matched with the push slide block 15312; the push rack 1522 is fixed on the push slide rail 15311; the push gear 1521 is rotatably mounted on the push mounting plate 151; the push gear 1521 is mounted at the output end of the push drive motor, and is engaged with the push rack 1522. The push component 1532 includes a push rod portion 15321 and a push locating element 15322 provided on the push rod portion 15321; the push rod portion 15321 is fixed on the push slide rail 15311. When the push mechanism 15 pushes a consumable box 2, the push locating element 15322 can match with a notch of the consumable box 2, so that the push mechanism 15 accurately is matched with the consumable box 2, thereby guaranteeing that the consumable box 2 is aligned with the consumable box positioning and dropping mechanism 14, and guaranteeing that the consumable box 2 is accurately located. When the consumable box 2 is pushed, the push drive motor drives the push gear 1521 to rotate; the push gear 1521 drives the push rack 1522 to move; then the push rack 1522 drives the push slide rail 15311 to move along the push slide block 15312; thus, the push slide rail 15311 drives the push rod portion 15321 to push the consumable box 2 at the top layer of the consumable box lifting mechanism 12 to the consumable box positioning and dropping mechanism 14.

Optionally, the push transmission component and the push sliding component 1531 can be a structure with cooperative gear transmission component, slide rail and slide block, and can also be a structure with cooperative synchronous belt, guide rail and slide block, a connecting rod structure, a screw rod structure, a stroke multiplying structure, a double platform output structure or any other structure that is able to push the consumable box 2 from the top layer of the consumable box lifting mechanism 12 to the consumable box positioning and dropping mechanism 14. Optionally, the push rod portion 15321 is a push plate, a push rod, a push block or any other structure that is able to push the consumable box 2. Optionally, the push locating element 15322 is a locating ball, a locating lug boss or any other structure that can play a locating role. Further, the push sliding component 1531 further includes a push barrier 15313; the push barrier 15313 is configured to locate the push mechanism 15. Preferably, the push barrier 15313 is an optical coupler barrier.

The consumable box automatic transmission device 1 of the present disclosure transmits the consumable box 2 to the consumable box lifting mechanism 12 through the consumable box storage mechanism 11; the consumable box lifting mechanism 12 lifts the consumable box 2 to the top layer of the consumable box lifting mechanism 12; the push mechanism 15 pushes the consumable box 2 to the consumable box positioning and dropping mechanism 14; the consumable box positioning and dropping mechanism 14 locates the consumable box 2. When the chemiluminescence detector grabs the consumables in the consumable box 2, the push mechanism 15 is reset; the consumable box positioning and dropping mechanism 14 does not support the consumable box 2; the consumable box 2 drops into the consumable box recycling mechanism 13, and is stored in the consumable box recycling mechanism 13. Then the consumable box lifting mechanism 12 again lifts the consumable box at the lesser top layer to the top layer, and the push mechanism 15 again pushes the consumable box 2 to the consumable box positioning and dropping mechanism 13; such operation is repeated; when the consumable boxes 2 in the consumable box lifting mechanism 12 are used up or have a small amount, the consumable box lifting mechanism 12 receives the consumable boxes 2 conveyed by the consumable box storage mechanism 11 at the transmission position of the consumable box storage mechanism 11; when the consumable boxes 2 in the consumable box storage mechanism 11 have a small amount or are used up, consumable boxes are loaded into the consumable box storage mechanism 11; when the number of the used consumable boxes 2 is relatively large in the consumable box recycling mechanism 13, the consumable boxes 2 can be taken out at the lower part of the consumable box recycling mechanism 13. In this way, automatic operation of the consumable box automatic transmission device 1 is implemented, and the consumable boxes 2 are continuously loaded and discharged, thereby improving overall efficiency.

Referring to FIG. 1 to FIG. 3, optionally, the consumable box automatic transmission device 1 further includes a drawer mechanism 16; the consumable box storage mechanism 11 is provided in the drawer mechanism 16; the drawer mechanism 16 is able to drive the consumable box storage mechanism 11 to move, so that the consumable box storage mechanism 11 is abutted with or separated from the consumable box lifting mechanism 12. The drawer mechanism 16 is configured to pull and push the consumable box storage mechanism 11. When the drawer mechanism 16 is pulled, the consumable box storage mechanism 11 is separated from the consumable box lifting mechanism 12, and a consumable box 2 can be loaded into the consumable box storage mechanism 11; when the drawer mechanism 16 is pushed, the consumable box storage mechanism 11 is able to transmit the consumable box 2 to the consumable box lifting mechanism 12. Optionally, the drawer mechanism 16 can be pulled manually or via automatic control. Of course, in other embodiments of the present disclosure, the consumable box storage mechanism 11 can also be abutted with the consumable box lifting mechanism 12 all the time, when the loading of the consumable box 2 can be implemented by opening and closing a door. When a compartment door of the consumable box storage mechanism 11 is opened, a consumable box 2 can be loaded into the consumable box storage mechanism 11; when the loading is finished, the compartment door of the consumable box storage mechanism 11 is closed, and the consumable box storage mechanism 11 is able to transmit the consumable box 2 to the consumable box lifting mechanism 12.

When the consumable boxes 2 in the consumable box storage mechanism 11 are fully or partially conveyed to the consumable box lifting mechanism 12, the consumable box storage mechanism 11 needs to supplement consumable boxes 2; when the consumable box storage mechanism 11 is pulled, the consumable box storage mechanism 11 is separated from the consumable box lifting mechanism 12; then, if a few consumable boxes 2 are left in the consumable box lifting mechanism 12 or unused consumable boxes 2 remain at the preset position, the instrument can still run properly; the user can add consumable boxes 2 to the consumable box storage mechanism 11; when the adding is finished, the consumable box storage mechanism 11 is pushed; thus, the consumable box storage mechanism 11 is abutted with the consumable box lifting mechanism 12, and the consumable box storage mechanism 11 can continue to convey the consumable boxes 2 to the consumable box lifting mechanism 12. In this way, the consumable box lifting mechanism 12 can convey the consumable boxes 2 all the time without interruption, thereby implementing continuous loading of the consumable boxes 2, and improving working efficiency of the chemiluminescence detector.

Further, the recycling storage structure includes a first recycling storage structure 131 and a second recycling storage structure 132; the first recycling storage structure 131 is located above the second recycling storage structure 132. The second recycling storage structure 132 is movably abutted with or separated from the first recycling storage structure 131. When the second recycling storage structure 132 is separated from the first recycling storage structure 131, the consumable boxes 2 in the second recycling storage structure 132 can be taken out, so as to prevent the operation of the chemiluminescence detector from being affected by the consumable box recycling mechanism 13 full of the consumable boxes 2. When the first recycling storage structure 131 is abutted with the second recycling storage structure 132, the consumable boxes 2 can be stored in the second recycling storage structure 132. Besides, the recycling transmission structure 133 is provided in the first recycling storage structure 131 and the second recycling storage structure 132, and can move between the top layer of the first recycling storage structure 131 and the bottom of the second recycling storage structure 132.

When the second recycling storage structure 132 is fully or partially filled with consumable boxes 2, the consumable boxes 2 in the second recycling storage structure 132 need to be taken out; the second recycling storage structure 132 is pulled, and is separated from the first recycling storage structure 131; then the consumable boxes 2 in the second recycling storage structure 132 can be taken out; then, the second recycling storage structure 132 is pushed, and is abutted with the first recycling storage structure 131; the consumable box positioning and dropping mechanism 14 can continue to convey empty consumable boxes 2 to the second recycling storage structure 132 through the first recycling storage structure 131. In this way, the used consumable boxes 2 can be stored continuously, and the working efficiency of the chemiluminescence detector is improved.

Preferably, the second recycling storage structure 132 is provided with a recycling rise-fall component; the recycling rise-fall component is able to drive the consumable boxes 2 in the second recycling storage structure 132 to rise or fall. When the second recycling storage structure 132 is separated from the first recycling storage structure 131, the recycling rise-fall component is able to push out the consumable boxes 2 in the second recycling storage structure 132, and the operator can remove the consumable boxes 2. Of course, in another embodiment of the present disclosure, the second recycling storage structure 132 can also be provided with a recycling basket; multiple consumable boxes 2 are stored in the recycling basket; the consumable boxes 2 are taken out by wholly taking the recycling basket out. In other embodiments of the present disclosure, the consumable boxes 2 in the second recycling storage structure 132 can also be taken out by opening and closing a door. When a compartment door of the second recycling storage structure 132 is opened, the consumable boxes 2 in the second recycling storage structure 132 scan be taken out; when the consumable boxes 2 are removed, the compartment door of the second recycling storage structure 132 is closed; then the first recycling storage structure 131 can normally recycle consumable boxes 2.

The chemiluminescence detector is provided with a mounting platform 3 for mounting the consumable box lifting mechanism 12 and the first recycling storage structure 131; the mounting platform 3 is located above the drawer mechanism 16; the drawer mechanism 16 can be pulled and pushed relative to the mounting platform 3. The consumable box storage mechanism 11 and the second recycling storage structure 132 are mounted on the drawer mechanism 16; the drawer mechanism 16 is able to drive the consumable box storage mechanism 11 and the second recycling storage structure 132 on the drawer mechanism 16 to be pulled from the chemiluminescence detector, so that the consumable box storage mechanism 11 is separated from the consumable box lifting mechanism 12, and the second recycling storage structure 132 is separated from the first recycling storage structure 131; then, consumable boxes 2 containing consumables can be added into the consumable box storage mechanism 11, and empty consumable boxes 2 can be taken out of the second recycling storage structure 132; then the drawer mechanism 16 is pushed into the chemiluminescence detector; the consumable box storage mechanism 11 is abutted with the consumable box lifting mechanism 12, and the second recycling storage structure 132 is abutted with the first recycling storage structure 131; the consumable boxes 2 in the consumable box storage mechanism 11 can be conveyed to the consumable box lifting mechanism 12, and the consumable boxes 2 in the first recycling storage structure 131 can be stored in the second recycling storage structure 132.

The present disclosure further provides a consumable box automatic transmission method, which is applied to the consumable box automatic transmission device 1 in the above embodiments and includes the following steps.

A consumable box storage mechanism 11 drives consumable boxes 2 to rise and move to the bottom of a consumable box lifting mechanism 12.

The consumable box lifting mechanism 12 receives the consumable boxes 2 at a bottom.

The consumable box lifting mechanism 12 transmits one of the consumable boxes 2 to the top layer of the consumable box lifting mechanism 12.

With the consumable box automatic transmission method of the present disclosure, the consumable box storage mechanism 11 and the consumable box lifting mechanism 12 is able to respectively transmit the consumable boxes 2. The consumable boxes 2 are provided in a laminated manner in the consumable box storage mechanism 11; the consumable box storage mechanism 11 is able to drive multiple consumable boxes 2 to rise together. The consumable box storage mechanism 11 transmits the highest one of the consumable boxes 2 therein upward, so that the highest one of the consumable boxes 2 in the consumable box storage mechanism 11 is located at a transmission position, and the consumable box lifting mechanism 12 receives the consumable boxes 2 at the transmission position; after reception, the consumable box lifting mechanism 12 moves upward, the consumable box storage mechanism 11 moves upward and transmits consumable boxes 2 to the transmission position, and the consumable box lifting mechanism 12 again receives the consumable boxes 2 at the transmission position; through such repeated operation, the consumable box lifting mechanism 12 gradually rises and receives the consumable boxes 2; the consumable box lifting mechanism 12 stops moving, upward when the highest one of the consumable boxes 2 in the consumable box lifting mechanism 12 is moved to a lesser top layer of the consumable box lifting mechanism 12; the consumable box storage mechanism 11 stops conveying consumable boxes 2 to the transmission position. When the consumable box automatic transmission device 1 conveys the consumable boxes 2 to a preset position, the consumable box lifting mechanism 12 lifts the consumable boxes 2 from the lesser top layer to a top layer; the push mechanism 15 pushes a consumable box 2 at the top layer of the consumable box lifting mechanism 12 to the consumable box positioning and dropping mechanism 14; the chemiluminescence detector grabs the consumables in the consumable boxes 2 at the consumable box positioning and dropping mechanism 14; when needing to convey the consumable boxes 2 to the consumable box positioning and dropping mechanism 14 again, the consumable box lifting mechanism 12 lifts a consumable box 2 at the lesser top layer to the top layer; through such repetition, when the consumable boxes 2 in the consumable box lifting mechanism 12 are used up or have a small amount, the consumable box lifting mechanism 12 loads the consumable boxes 2 again. In this way, a consumable box 2 can be continuously loaded under the consumable boxes 2, thereby implementing the continuous conveyance of the consumable boxes 2, and improving the efficiency.

Further, before the step that the consumable box storage mechanism 11 drives the consumable boxes 2 to rise to the bottom of the consumable box lifting mechanism 12, the consumable box automatic transmission method further includes the following steps.

Multiple consumable boxes 2 are loaded into the consumable box storage mechanism 11.

The consumable box storage mechanism 11 drives multiple consumable boxes 2 to move till the highest one of the consumable boxes 2 of multiple consumable boxes 2 are located at a bottom of the consumable box lifting mechanism 12.

Before the consumable box storage mechanism 11 conveys the consumable boxes 2 to the consumable box lifting mechanism 12, the consumable boxes 2 are loaded into the consumable box storage mechanism 11; after loading, the consumable box storage mechanism 11 is controlled to drive the consumable boxes 2 to move upward, so that the consumable boxes 2 are lifted to the bottom of the consumable box lifting mechanism 12, namely the transmission position, thereby providing convenience for the consumable box lifting mechanism 12 to receive the consumable boxes 2. It may be understood that, before the consumable box storage mechanism 11 transmits the consumable boxes 2 to the transmission position, the consumable box lifting mechanism 12 makes preparations at the transmission position; when the consumable box storage mechanism 11 conveys the consumable boxes 2 to the transmission position, the consumable box lifting mechanism 12 can receive the consumable boxes at the transmission position. It is to be noted that the consumable boxes 2 can be loaded into the consumable box storage mechanism 11 by pulling the consumable box storage mechanism 11, or the consumable boxes 2 can be loaded into the consumable box storage mechanism 11 by opening and closing a door.

Preferably, the consumable box automatic transmission method further includes a step that the consumable boxes 2 are loaded into the consumable box storage mechanism 11 and includes the following steps.

The storage transmission structure 111 is controlled to rise or fall along the height direction of the consumable box storage mechanism 11 according to a detection signal sent by a first storage detection unit 1141.

The storage transmission structure 111 is controlled to move upward for one layer along the height direction of the consumable box storage mechanism 11 whenever the first storage detection unit 1141 does not detect any consumable box 2.

If the first storage detection unit 1141 does not detect any consumable box 2 all the time and the storage transmission structure 111 moves to the top layer of the consumable box storage mechanism 11, the storage transmission structure 111 stops moving, and the consumable boxes 2 are loaded onto the storage transmission structure.

Whenever the first storage detection unit 1141 detects the consumable boxes 2, the storage transmission structure 111 is controlled to move downward for one layer along the height direction of the consumable box storage mechanism 11, and the consumable boxes are loaded onto the storage transmission structure.

The consumable box automatic transmission device 1 can implement loading of consumable boxes 2 through the above operation step; when the consumable boxes 2 are loaded into the consumable box storage mechanism 11, the storage transmission structure 111 moves upward; if the first storage detection unit 1141 does not detect any consumable box 2 on a storage support portion 1112, a storage rise-fall component 1111 continuously drives the storage support portion 1112 to rise; the storage rise-fall component 1111 stops driving the storage support portion 1112 to rise when the storage support portion 1112 is located at the top layer of a storage frame structure 112; then the storage support portion 1112 is at a loading position, and the consumable boxes 2 can be loaded onto the storage support portion 1112.

If the first storage detection unit 1141 detects the consumable boxes 2 on the storage support portion 1112, the consumable boxes 2 are at the loading position; then the storage rise-fall component 1111 drives the storage support portion 1112 to fall for one layer, so that the loading position is vacated, and the consumable boxes can be loaded to the loading position. Besides, when the consumable boxes 2 are loaded, the storage transmission structure 111 automatically falls for one layer if the first detection unit detects a consumable box 2, thereby vacating the top layer for an operator for continuous loading. Thus, when the consumable box storage mechanism 11 loads the consumable boxes 2 at the top layer, the operator can always maintain a proper posture to load the consumable boxes 2 without squatting, thereby saving energy and operating conveniently.

Further, the consumable box automatic transmission method further includes a step that the consumable boxes 2 are loaded into the consumable box storage mechanism 11 and further includes the following steps.

The storage transmission structure 111 is controlled to rise or fall along the height direction of the consumable box storage mechanism 11 according to a detection signal sent by a second storage detection unit 1142.

The storage transmission structure 111 is controlled to stop moving whenever the second storage detection unit 1142 detects a consumable box 2.

The storage transmission structure 111 is controlled to move upward for one layer along the height direction of the consumable box storage mechanism 11 whenever the second storage detection unit 1142 does not detect any consumable box 2.

The consumable box storage mechanism 11 implements loading of the consumable boxes 2 through the first storage detection unit 1141 and the second storage detection unit 1142. Specifically, the first storage detection unit 1141 and the second storage detection unit 1142 can control the storage rise-fall component 1111 of the storage rise-fall structure 111 to drive the storage support portion 1112 to rise or fall; if no consumable box 2 exists on the storage support portion 1112, the storage rise-fall component 1111 drives the storage support portion 1112 to move to the top layer of the storage frame structure 112, and the consumable boxes 2 are directly loaded to the storage support portion 1112. If the consumable box 2 exists on the storage support portion 1112, the storage rise-fall component 1111 drives the storage support portion 1112 to rise; when the second storage detection unit 1142 detects the consumable box 2, the storage rise-fall component 1111 drives the storage support portion 1112 to stop moving; then the consumable box 2 is under the loading position; no consumable box 2 is at the locating position, and the consumable box 2 can be loaded. Besides, when the first storage detection unit 1141 detects a consumable box 2, the storage rise-fall component 1111 drives the storage support portion 1112 to fall for one layer, so that the loading position is vacated, and the consumable box 2 can be continuously loaded; when the first storage detection unit 1141 detects a consumable box 2, the storage rise-fall component 1111 drives the storage support portion 1112 to fall for one layer; then if the second storage detection unit 1142 does not detect any consumable box 2, the storage rise-fall component 1111 drives the storage support portion 1112 to rise for one layer; a wrong operation may exist. In addition, if the storage rise-fall component 1111 drives the storage support portion 1112 to return to the bottom, the consumable box storage mechanism 11 is full, and the loading of the consumable boxes 2 can be stopped; of course, an arbitrary number of consumable boxes 2, lower than or equal to the storage capacity of the consumable box storage mechanism 11, can be loaded.

Furthermore, after the storage transmission structure 111 moves to the bottom of the storage frame structure 112 and the second storage detection unit 1142 detects a consumable box 2, the loading of the consumable boxes 2 to the consumable box storage mechanism 11 is stopped, indicating that the consumable box storage mechanism 11 is full of the consumable boxes 2; thus, the first storage detection unit 1141 can detect no consumable box 2 at the top layer of the consumable box storage mechanism 11, thereby preventing the top layer of the consumable box storage mechanism 11 with the consumable box 2 from contacting and interfering with other structures of the chemiluminescence detector.

Further, when the consumable box lifting mechanism 12 transmits a consumable box 2 to the top layer of the consumable box lifting mechanism 12, a consumable box 2 can be loaded into the consumable box storage mechanism 11. It may be understood that, when the chemiluminescence detector operates, if there are few consumable boxes 2 in the consumable box storage mechanism 11 or all are conveyed to the consumable box lifting mechanism 12, as the consumable box storage mechanism 11 and the consumable box lifting mechanism 12 move independently, a consumable box 2 can be loaded into the consumable box storage mechanism 11, without affecting the movement of the consumable box lifting mechanism 12; thus, the consumable box lifting mechanism 12 can continue to lift the consumable boxes 2, and the operational efficiency of the chemiluminescence detector is improved.

Optionally, the consumable box automatic transmission method further includes a step that the consumable box storage mechanism 11 executes a counting operation and includes the following steps.

The storage transmission structure 111 is controlled to fall along the height direction of the consumable box storage mechanism 11 till the storage transmission structure 111 moves to the bottom of the consumable box storage mechanism 11 and the storage transmission structure 111 stops moving.

The storage transmission structure 111 is controlled to rise along the height direction of the consumable box storage mechanism 11 till the second storage detection unit 1142 detects a consumable box 2 or the storage transmission structure 111 moves to the lesser top layer of the storage transmission structure 111 and the storage transmission structure 111 stops moving.

The actual number of the consumable boxes 2 in the consumable box storage mechanism 11 under the current status is calculated according to the number of layers the storage transmission structure 111 moves and the storage capacity of the consumable box storage mechanism 11.

The consumable box automatic transmission method can further implement counting of the actual number of the consumable boxes 2 in the consumable box storage mechanism 11. When the number of the consumable boxes 2 in the consumable box storage mechanism 11 needs to be counted, the storage rise-fall component 1111 of the storage transmission structure 111 is able to drive the storage support portion 1112 to fall to the bottom of the storage frame structure 112; then the storage rise-fall component 1111 again drives the storage support portion 1112 to move upward; and the storage rise-fall component 111 stops moving upward when the second storage detection unit 1142 detects the consumable boxes 2 on the storage support portion 1112. At this moment, according to the number of layers that the storage support portion 1112 moves upward and the storage capacity of the consumable boxes 2 stored in the storage frame structure 112 of the consumable box storage mechanism 2, the actual number of the consumable boxes 2 in the storage frame structure 112 under current status is calculated.

Further, the consumable box lifting mechanism 12 includes a lifting transmission structure 121 configured to lift the consumable boxes 2 and a lifting detection structure 124; the lifting detection structure 124 includes a first lifting detection unit 1242 and a second lifting detection unit 1243; the first lifting detection unit 1242 is arranged at the top layer of the consumable box lifting mechanism 12; the second lifting detection unit 1242 is arranged at a bottom of the consumable box lifting mechanism 12; and the consumable box automatic transmission method further includes a step that the consumable box lifting mechanism 12 executes a counting operation and includes the following steps.

The lifting transmission structure 121 is controlled to move upward along the height direction of the consumable box lifting mechanism 12.

The lifting transmission structure 121 is controlled to move downward along the height direction of the consumable box lifting mechanism 12 if the first lifting detection unit 1242 detects one or more consumable boxes 2.

The lifting transmission structure 121 is controlled to stop moving if the second lifting detection unit 1242 detects the consumable boxes 2.

The actual number of the consumable boxes 2 in the consumable box lifting mechanism 12 under the current status is calculated according to the number of layers the lifting transmission structure 121 moves from the first lifting detection unit 1242 to the second lifting detection unit 1242 and the storage capacity of the consumable box lifting mechanism 12.

The consumable box automatic transmission method can further implement counting of the actual number of the consumable boxes 2 in the consumable box lifting mechanism 12. Before every count, a control device of the chemiluminescence detector can control the rotating components 1211 of the lifting transmission structure 121 to wholly move upward layer by layer till the first lifting detection unit 1242 detects a consumable box 2; then, the rotating components 1211 are wholly driven to move downward layer by layer till the second lifting detection unit 1243 detects a consumable box 2; according to the number of layers the rotating components move downward and the number of consumables stored in the consumable box lifting mechanism 12, the number of the consumable boxes 2 in the consumable box lifting mechanism 12 is calculated; then according to the maximum number of the consumables stored in each consumable box 2, the total number of the consumables is calculated.

Further, the step that the consumable box lifting mechanism 12 executes a counting operation further includes the following steps.

The first lifting detection unit 1242 does not detect any consumable box 2 when the lifting transmission structure 121 moves from the bottom of the consumable box lifting mechanism 12 to the top layer.

Or, the second lifting detection unit 1242 does not detect any consumable box 2 when the lifting transmission structure 121 moves from the top layer of the consumable box lifting mechanism 12 to the bottom.

The number of the consumable boxes in the consumable box lifting mechanism 12 is zero.

If the first lifting detection unit 1242 does not detect any consumable box 2 all the time when the lifting transmission structure 121 moves from the bottom of the lifting frame structure 122 to the top layer of the lifting frame structure 122, it is indicated that no consumable box 2 exists in the consumable box lifting mechanism 12. If the second lifting detection unit 1243 does not detect any consumable box 2 all the time when the lifting transmission structure 121 moves from the top layer of the lifting frame structure 122 to the bottom of the lifting frame structure 122, it is indicated that no consumable box 2 exists in the consumable box lifting mechanism 12. In this way, the lifting transmission structure 121 can be prevented from idling, thereby guaranteeing the operational performance.

The present disclosure further provides a chemiluminescence detector, including a sample adding device, a reaction device, a cleaning device, a luminescence detection device, a control device and a consumable box automatic transmission device 1 in the above embodiments. The consumable box automatic transmission device 1 is able to transmit each of consumable boxes 2 to a preset position; the control device sequentially moves consumables in the consumable boxes 2 to the sample adding device, the reaction device, the cleaning device and the luminescence detection device. The chemiluminescence detector of the present disclosure can implement continuous loading and parallel conveyance of consumable boxes 2 through the consumable box automatic transmission device 1, and grabbing of consumables by conveying each of the consumable boxes 2 to a preset position, namely a consumable box positioning and dropping mechanism 14, thereby implementing automatic conveyance of the consumables, and improving the operational efficiency of the chemiluminescence detector. Besides, the consumable box automatic transmission device 1 can further store the consumable boxes 2 in laminated and layered manners, so the large capacity storage of the consumable boxes 2 is implemented, and the occupancy in the layout position of the instrument is minimized; therefore, the structure of the consumable box automatic transmission device 1 is compact, and the overall size of the chemiluminescence detector is reduced.

Each technical characteristic of the above embodiments may be combined freely. To describe concisely, all possible combinations for the each technical characteristic of the above embodiments are not described. However, as long as there is no conflict among the combinations of these technical characteristics, all should be considered as a recording scope of the specification.

The above embodiments are only several embodiments of the present disclosure and are described concretely in detail, and therefore, should not be understood as limits to scope of the present disclosure. It should be noted that, those of ordinary skill in the art may further make several alternations and improvements without departing from the concept of the present disclosure, and all should pertain to the scope of protection of the present disclosure. Therefore, the scope of protection of the present disclosure should be subjected to the appended claims.

What is claimed is:

1. A consumable box automatic transmission device, comprising:
   a consumable box storage mechanism, configured to load and store consumable boxes; and
   a consumable box lifting mechanism, located above the consumable box storage mechanism, wherein the consumable box lifting mechanism is able to lift the consumable boxes;
   wherein the consumable box storage mechanism and the consumable box lifting mechanism is able to respectively store and transmit the consumable boxes; the consumable box storage mechanism is able to transmit the consumable boxes to the bottom of the consumable box lifting mechanism; and the consumable box lifting mechanism receives the consumable boxes at a bottom and lifts the consumable boxes to a top layer of the consumable box lifting mechanism;

the consumable box lifting mechanism comprises a lifting transmission structure and a lifting frame structure and a lifting drive structure, the lifting transmission structure can support multiple consumable boxes therein in a layered manner and is able to drive the multiple consumable boxes to move synchronously, the lifting drive structure is provided on the lifting frame structure; the lifting drive structure is in transmission connection with the lifting transmission structure, the lifting transmission structure is provided in the lifting frame structure in a rise-fall manner; the lifting drive structure drives the lifting transmission structure, thereby driving multiple consumable boxes to rise or fall in the lifting frame structure, the lifting transmission structure comprises two rotating components and multiple rotating support portions; the two rotating components are symmetrically arranged in the lifting frame structure; multiple rotating support portions are respectively provided on the two rotating components, and multiple rotating support portions on each rotating component are arranged intervals along a rise-fall direction; the lifting drive structure drives the rotating components, thereby driving multiple rotating support portions to move synchronously; and the rotating support portions respectively drive the consumable boxes supported by the rotating support portions to rise or fall, wherein the two rotating components are respectively provided on two opposite sides of the lifting frame structure; two opposite rotating support portions on the two rotating components can support two ends of each of the consumable boxes:

the consumable box storage mechanism comprises a storage transmission structure; and the storage transmission structure drives the multiple consumable boxes to rise, and conveys the consumable boxes to the lifting transmission structure; and the storage transmission structure is able to store the multiple consumable boxes placed in a laminated manner, and drive the multiple consumable boxes to move synchronously, and is able to transmit the consumable boxes to the lifting transmission structure one by one.

2. The consumable box automatic transmission device as claimed in claim 1, wherein the consumable box storage mechanism comprises a storage frame structure and a storage drive structure; the storage drive structure is provided on the storage frame structure; the storage transmission structure is provided in the storage frame structure in a rise-fall manner; the storage drive structure is in transmission connection with the storage transmission structure; and the storage drive structure drives the storage transmission structure, thereby driving multiple consumable boxes to rise or fall in the storage frame structure, the storage drive structure comprises a storage drive motor and a storage output component; the storage drive motor is fixed on the storage frame structure, and the storage output component is in transmission connection with the storage transmission structure.

3. The consumable box automatic transmission device as claimed in claim 2, wherein the storage transmission structure comprises a storage rise-fall component and a storage support portion provided on the storage rise-fall component; the storage rise-fall component is movably provided on the storage frame structure;

multiple consumable boxes are able to be provided on the storage support portion in a laminated manner; and the storage drive structure drives the storage rise-fall component, thereby driving the storage support portion to rise or fall.

4. The consumable box automatic transmission device as claimed in claim 2, wherein the consumable box storage mechanism further comprises a storage detection structure; the storage detection structure is provided in the storage frame structure;

the storage detection structure comprises a first storage detection unit;
a detection area of the first storage detection unit is located at a top layer of the storage frame structure; and the first storage detection unit is able to detect whether there are one or more consumable boxes in the detection area.

5. The consumable box automatic transmission device as claimed in claim 1, wherein the lifting frame structure comprises a lifting border component and multiple lifting surrounding plates; the lifting drive structure is mounted on the lifting border component; the lifting transmission structure is mounted in the lifting border component; and the multiple lifting surrounding plates are arranged oppositely on two sides of the lifting border component.

6. The consumable box automatic transmission device as claimed in claim 4, wherein the storage detection structure further comprises a second storage detection unit; the second storage detection unit is provided on the storage frame structure; and a detection area of the second storage detection unit is located under the detection area of the first storage detection unit, wherein a movement distance that the storage transmission structure moves from the detection area of the second storage detection unit to the detection area of the first storage detection unit is a height of one consumable box along a rise-fall direction.

7. The consumable box automatic transmission device as claimed in claim 1, wherein each of the rotating components comprises a rotating belt and two rotating shafts, the two rotating shafts are rotatably provided on the lifting frame structure, and one end of one rotating shaft stretches out of the lifting frame structure and is in transmission connection with the lifting drive structure; and the lifting drive structure drives the rotating shafts, thereby driving the rotating belts to rotate, wherein the multiple rotating support portions are uniformly arranged along the periphery of the two rotating belts; and the rotating support portions at corresponding positions on the two rotating belts are arranged in a coplanar manner.

8. The consumable box automatic transmission device as claimed in claim 1, wherein the consumable box lifting mechanism further comprises a lifting detection structure; the lifting detection structure is provided on the lifting frame structure;

the lifting detection structure comprises a lifting locating unit; the lifting locating unit is provided on the lifting frame structure; and the lifting locating unit is matched with the rotating support portions, and carries out initial location to the rotating support portions.

9. The consumable box automatic transmission device as claimed in claim 8, wherein the lifting detection structure further comprises a first lifting detection unit; a detection area of the first lifting detection unit is located at a top layer of the lifting frame structure; the rotating components drive the rotating support portions to move to the detection area of the first lifting detection unit; and the first lifting detection unit is able to detect whether there are one or more consumable boxes on the rotating support portions in the detection area.

10. The consumable box automatic transmission device as claimed in claim 9, wherein the lifting detection structure further comprises a second lifting detection unit; a detection area of the second lifting detection unit is located at a bottom layer of the lifting frame structure; the rotating components drive the rotating support portions to move to the detection area of the second lifting detection unit; and the second lifting detection unit is able to detect whether there are one or more consumable boxes on the rotating support portions in the detection area.

11. The consumable box automatic transmission device as claimed in claim 1, wherein the consumable box automatic transmission device further comprises a drawer mechanism, the consumable box storage mechanism is provided in the drawer mechanism; and the drawer mechanism is able to drive the consumable box storage mechanism to move, so that the consumable box storage mechanism is abutted with or separated from the consumable box lifting mechanism.

12. The consumable box automatic transmission device as claimed in claim 1, wherein the consumable box automatic transmission device further comprises a push mechanism, the push mechanism is provided on the consumable box lifting mechanism; and the push mechanism is able to push each of the consumable boxes at the top layer of the consumable box lifting mechanism to a preset position.

13. The consumable box automatic transmission device as claimed in claim 12, wherein the consumable box automatic transmission device further comprises a consumable box recycling mechanism, the consumable box recycling mechanism is located under the preset position; and the consumable box recycling mechanism is able to recycle each of the consumable boxes at the preset position, the consumable box recycling mechanism comprises a recycling storage structure and a recycling transmission structure; the recycling transmission structure is movably provided in the recycling storage structure.

14. A consumable box automatic transmission method, where applying to a consumable box automatic transmission device, the consumable box automatic transmission device comprising a consumable box storage mechanism and a consumable box lifting mechanism, the consumable box storage mechanism being capable of conveying consumable boxes to the consumable box lifting mechanism, the consumable box storage mechanism comprises a storage detection structure and a storage transmission structure configured to transmit the consumable boxes; the storage detection structure comprises a first storage detection unit; the first storage detection unit is located at a top layer of the consumable box storage mechanism; and the consumable box automatic transmission method comprising the following steps:

the consumable box storage mechanism drives each of the consumable boxes to rise and move to the bottom of the consumable box lifting mechanism;
the consumable box lifting mechanism receives the consumable boxes at a bottom; and
the consumable box lifting mechanism transmits the consumable boxes to a lesser top layer of the consumable box lifting mechanism;
the consumable box automatic transmission method further comprises a step of loading the consumable boxes into the consumable box storage mechanism and comprises the following steps:
controlling the storage transmission structure to rise or fall along a height direction of the consumable box storage mechanism according to a detection signal sent by the first storage detection unit;
controlling the storage transmission structure to move upward for one layer along the height direction of the consumable box storage mechanism whenever the first storage detection unit does not detect any consumable box:
if the first storage detection unit does not detect any consumable box all the time and the storage transmission structure moves to the top layer of the consumable box storage mechanism, controlling the storage transmission structure to stop moving, and loading the consumable boxes onto the storage transmission structure; and
whenever the first storage detection unit detects one or more consumable boxes, controlling the storage transmission structure to move downward for one layer along the height direction of the consumable box storage mechanism, and loading the consumable boxes onto the storage transmission structure.

15. The consumable box automatic transmission method as claimed in claim 14, wherein the storage detection structure further comprises a second storage detection unit; the second storage detection unit is located at a lesser top layer of the consumable box storage mechanism; and the consumable box automatic transmission method further comprises a step of loading the consumable boxes into the consumable box storage mechanism and further comprises the following steps:
controlling the storage transmission structure to rise or fall along the height direction of the consumable box storage mechanism according to a detection signal sent by the second storage detection unit;
controlling the storage transmission structure to stop moving whenever the second storage detection unit detects one or more consumable boxes; and
controlling the storage transmission structure to move upward for one layer along the height direction of the consumable box storage mechanism whenever the second storage detection unit does not detect any consumable box.

* * * * *